United States Patent
Tendler et al.

(10) Patent No.: US 9,670,256 B2
(45) Date of Patent: *Jun. 6, 2017

(54) SYNTHETIC ACTIVE PEPTIDE FRAGMENTS

(71) Applicant: Fundaçao Oswaldo Cruz—FIOCRUZ, Manguinhos (BR)

(72) Inventors: Miriam Tendler, Rio de Janeiro (BR); Richard Charles Garratt, Sao Paulo (BR); Naftale Katz, Minas Gerais (BR); Andrew John George Simpson, Sao Paulo (BR); Frank Jefferson Alarcon de Barrientos, Rio de Janeiro (BR); Mônica Magno Vilar, Rio de Janeiro (BR); Marilia Sirianni dos Santos Almeida, Santa Catarina (BR)

(73) Assignee: Fundacao Oswaldo Cruz-FIOCRUZ, Rio de Janiero (BR)

( * ) Notice: Subject to any disclaimer, the term of this patent is extended or adjusted under 35 U.S.C. 154(b) by 0 days.

This patent is subject to a terminal disclaimer.

(21) Appl. No.: 14/539,248

(22) Filed: Nov. 12, 2014

(65) Prior Publication Data

US 2015/0064211 A1 Mar. 5, 2015

Related U.S. Application Data

(62) Division of application No. 13/666,937, filed on Nov. 1, 2012, now Pat. No. 8,909,483, which is a division of application No. 12/350,945, filed on Jan. 8, 2009, now Pat. No. 8,321,143, which is a division of application No. 11/005,566, filed on Dec. 7, 2004, now abandoned, which is a division of application No. 10/113,946, filed on Apr. 2, 2002, now abandoned.

(51) Int. Cl.
*A61K 39/00* (2006.01)
*C07K 14/435* (2006.01)
*G01N 33/68* (2006.01)

(52) U.S. Cl.
CPC .... *C07K 14/43559* (2013.01); *C07K 14/4354* (2013.01); *G01N 33/6893* (2013.01); *A61K 39/00* (2013.01); *C07K 2319/00* (2013.01)

(58) Field of Classification Search
None
See application file for complete search history.

(56) References Cited

U.S. PATENT DOCUMENTS 4,396,600 A 8/1983 Messineo et al.
5,019,383 A 5/1991 Hopp

FOREIGN PATENT DOCUMENTS

BR WO 03/082897 A2 * 9/2003
EP 0 251 933 A1 1/1988
WO WO 91/09621 7/1992
WO WO 93/23542 11/1993

OTHER PUBLICATIONS

Brito et al., "CD4+ T Cells of Schistosomiasis Naturally Resistant Individuals Living in an Endemic Area Produce Interferon-γ and Tumour Necrosis Factor-α in Response to the Recombinant 14$_{KDA}$ *Schistosoma mansoni* Fatty Acid-Binding Protein," *Scand. J. Immunol.*, 51: 595-601, 2000.
Brito et al., "Human IgG1 and IgG3 recognition of *Schistosoma mansoni* 14 kDa fatty acid-binding recombinant protein," *Parasite Immunology*, 22: 41-48, 2000.
Moser et al., "14-kDA *Schistosoma mansoni* Polypeptide is Homologous to a Gene Family of Fatty Acid Binding Proteins," *J. Biological Chem.* 266(13): 8447-8454, 1991.
Müller-Fahrnow et al., "Three-dimensional structure of fatty-acid-binding protein from bovine heart," *Eur. J. Biochem.* 199: 271-276, 1991.
Perez et al., "Cytogenetics as a Tool for Triatomine Species Distinction (Hemiptera-reduvidae)," *Mem. Inst. Oswaldo Cruz*, 87(3): 353-361, 1992.
Ramos et al., "r-Sm 14-pRSETA Efficacy in Experimental Animals," *Mem. Inst. Oswaldo-Cruz*, 96-Suppl.: 131-135, 2001.
Sacchettini et al., "The Structure of Crystalline *Escherichia coli*-derived Rat Intestinal Fatty Acid-binding Protein at 2.5A Resolution," *J. Bio. Chem.*, 263(12): 5815-5819, 1988.
Sibanda et al., "β-Hairpin families in globular proteins," *Nature*, 316(6024): 170-174, 1985.
Tendler et al., "Immunogenic and Protective Activity of an Extract of *Schistosoma mansoni*," *Mem. Inst. Oswaldo Cruz*, Rio de Janeiro, 77(3): 275-283, 1982.
Tendler et al., "The Presence of *Schistosoma mansoni* Antigens in Solutions Used for Storing Adult Worms," *Rev. Inst. Med. trop. Sao Paulo*, 21(6): 293-296, 1979.
Tendler et al., "A *Schistosoma mansoni* fatty acid-binding protein, Sm14, is the potential basis of a dual-purpose anti-helminth vaccine," *PNAS*, 93: 269-273, 1996.
Wilmot et al., "Analysis and Prediction of the Different Types of β-Turn in Proteins," *J. Mol. Biol.*, 203: 221-232, 1988.

* cited by examiner

*Primary Examiner* — Padma V Baskar
(74) *Attorney, Agent, or Firm* — Klarquist Sparkman, LLP

(57) ABSTRACT

The present invention relates to peptide fragments which have one or more shared and/or similar amino acid sequences to amino acid sequences of specific portions of the 14 kDa protein of *S. mansoni* (SM14) or related FABPs (Fatty Acid Binding Proteins), the peptide fragments functioning as continuous or discontinuous epitopic regions of the molecule or mimicking its biological activity. More particularly, the present invention relates to a method for constructing active peptide fragments, peptide fragments, immunogenic compositions and diagnostic kits using peptide fragments.

8 Claims, 17 Drawing Sheets

```
     β1            α1              α2
MSSFLGKWKLSESHNFDAVMSKLGVSWATRQIGNTVTPTVTFTMDGDKMTMLTESTFKNLSCTFKFGE
#               #       #             #$#       #$              #  #

β5          β6              β7            β8             β9         β10
EFDEKTSDGRNVKSVVEKNSESKLTQTQVDPKNTTVIVREVDGDTMKTTVTVGDVTAIRNYKRLS-
$           # ###       #$    #            # #   #    $  # ###   $
```

FIG. 14

```
E.granulosus   1   MEAFLGTWKMEKSEGFQKIMERLGVDFVTIKMCNIVKIPHLIVTDLGKKKYKMASESTFKITECSFKLGE
F.gigantica    1   ?????SWKYGDSEMMEAYLKKLCISSDMVDKILMAKPEFTFT-LEGMQNTIKMVSSLKTKITTFTFGE
F.hepatica     1   MADFVGSWKYGHSEMMEAYLKMEAYLKKIGVSEDMVDKILMAKPEFTFT-LEGMKMTIKMVSSLMIKITTFTFGE
S.japonicum    1   MSSFLGKWKLSESIHFDAVHSKLGVSMATMQIGNTVTFTVTFT-MQGDTMHLTESTFKNLSVTFKFGE
S.mansoni      1   MSSFLGKWKLSESIHFDAVHSKLAVSMATMQIGNTVTFQVTFT-MQGDRMTMLTESTFKNLSCTFKFGE
                          #               #  *                 *##  *#        # #  #
                          β1              α1        α2                 β2    β3         β4

E.granulosus  70   KFKEVIRFTRCHIEFMITVEN--GVMKIFQUDKTKVTYIENVEGMELKAFVKVDEVVCVRTYSKVA-
F.gigantica   69   EFKEETADGKTAHTTVTKDSESKHFQVTTGPEYTTMVIIEVGDKHLATMFVGDVKAVTTLLKA--
F.hepatica    69   EFEEETPLGKKVMTKVTKDGSESKATQVLKGPECITEVMIEVGDKNLATMFVGDVKAVTTLLKA--
S.japonicum   69   EFDEKTSDGRSVKSVVTKDSESKITMFQKUSKMTVIVMELVGDTHKTTVTVQDVTAIRNYKRL--
S.mansoni     69   ERDEKTSDCRNVKSVVERNSESKLFQTQVDPKMTVIVREVQGDTHKTTVTVGDVTAIRNYKHLS-
                          *   ###  #         *        #  #*    *     ####  $
                   β5       β6          β7                β8      β9          β10
```

SYNTHETIC ACTIVE PEPTIDE FRAGMENTS

CROSS REFERENCE TO RELATED APPLICATIONS

The present application is a divisional of U.S. application Ser. No. 13/666,937, filed Nov. 1, 2012, issue as U.S. Pat. No. 8,909,483 on Dec. 9, 2014, which is a divisional of U.S. application Ser. No. 12/350,945, filed Jan. 8, 2009, issued as U.S. Pat. No. 8,321,143 on Nov. 27, 2012, which is a divisional of U.S. application Ser. No. 11/005,566, filed Dec. 7, 2004, now abandoned, which is a divisional of U.S. application Ser. No. 10/113,946, filed Apr. 2, 2002, now abandoned. All of the above-listed applications are herein incorporated by reference in their entirety.

INCORPORATION-BY-REFERENCE OF MATERIAL SUBMITTED AS AN ASCII TEXT FILE

A Sequence Listing is submitted herewith as an ASCII compliant text file named "76531-04_ST25.txt", created on Nov. 6, 2014, and having a size of 26.8 KB, as permitted under 37 CFR 1.821(c). The material in the aforementioned file is hereby incorporated by reference in its entirety.

FIELD

The present invention relates to peptide fragments which have one or more shared and/or similar amino acid sequences to amino acid sequences of specific portions of the 14 kDa protein of *S. mansoni* (Sm14) or related FABPs (Fatty Acid Binding Proteins), the said peptide fragments functioning as continuous or discontinuous epitopic regions of the molecule or mimicking its biological activity. More particularly, the present invention relates to a method for constructing active peptide fragments, peptide fragments, immunogenic compositions and diagnostic test kits using said fragments.

BACKGROUND

Sm14, belonging to the family of Fatty Acid Binding Proteins (FABPs), is a cross reactive antigen showing a high level of protection against schistosomiasis and fasciolosis.

Pathogens are infectious organisms, such as bacteria, virus, protozoa, helminths, or any parasite which causes infectious diseases to the host generally by expressing specific antigens which are recognized by host immune systems as foreign and become the target of an immunological response to eliminate the infectious pathogen.

Typically, there are specific sites on antigens, the binding epitopes or just epitopes, which bind to a complementary portion of a cellular protein, i.e., the receptor site. Thus, pathogen antigens often bind to cellular receptors on a host's cell as part of the process of infection of the host by the pathogen. Similar complementarity exists between host antibodies raised against an antigen and the antigenic determinants of the antigen itself. These regions of the antigenic molecule, however, may be different from those important for host cell invasion. In order to immunize the host and reduce the effectiveness of the pathogen to mount a challenge to the host, a number of vaccination strategies have been devised.

Up to recently, as described in Institute of Medicine, "Vaccine supply and innovation", Washington, D.C.: National Academy Press (1985), several strategies have been employed to develop safe and effective vaccines consisting of live attenuated pathogens, killed pathogens, components of pathogens, or modified toxins (toxoids).

Vaccines against several pathogenic virus, bacteria, and protozoa, such as small pox, yellow fever, measles, diphtheria and malaria are available. Concerning pathogenic helminths which are parasitic worms and cause human and veterinary diseases, such as schistosomiasis and fasciolosis, at the moment, no vaccines are currently used in prevention and control programmes. These diseases are not directly transmittable from one person (or animal) to another and the helminth requires an intermediate host and environmental conditions to complete its complex life cycle. There is still a great gap in the knowledge of the variables influencing the dynamics of transmission of these diseases in connection with vaccines and vaccination protocol design. In other words, and based on the current knowledge of epidemiological parameters which modulate and influence vaccination efficacy against these diseases, it can be asserted that neither the preferential individual levels of protection required by a vaccine, nor the number of individuals to be vaccinated and/or protected among a given population have yet been established.

Nowadays, the use of vaccines composed of pathogen components or attenuated parasites for human immunization is considered impractical and potentially dangerous. The worry in using such complex and undefined mixtures comes from the fact that the majority of components stimulate non-functional immune responses and some components can even be detrimental to vaccinated subjects, when toxic products of lipid peroxidation can be generated by immune attack against other parasite antigens, particularly surface antigens.

These considerations have led researchers to seek alternative methods for effective immunization and a great deal of effort has been made to purify natural proteins from natural sources or synthetically produce them by chemical means or alternatively by using recombinant DNA technology.

Attempts to vaccinate model animals against schistosomiasis with homogenates led researchers to find a saline extract (SE) which presented good results in conferring protection against diseases caused by *Schistosoma* infections in humans.

Protective immunity against schistosomes, was reported on the use of a "cocktail" of schistosome components (called SE) released early during the incubation of live and freshly perfused *S. mansoni* adult worm in phosphate buffered saline (PBS). Focusing on attempts to achieve protection against cercarial infection by vaccination, an experimental model was designed, in two different outbred animal hosts, the SW mouse and NZ rabbit, known to be fully susceptible and partially resistant to *S. mansoni* infection respectively.

Studies on the induced immune response in vaccinated animals aiming at the identification of the functionally relevant SE protective components, the site and mechanism of parasite death as well as markers of protection, have been the focus of our efforts in recent years. Less information on the molecular composition of SE, as well as on the identification and isolation of its protective components has been available until recently. (see: Tendler, M. and Scapin, M. (1979). "The presence of *Schistosoma mansoni* antigens in solutions used for storing adult worms". Rev. Inst. Med. Trop. 21(6): 293-296; Tendler, M et al. (1982). "Immunogenic and protective activity of an extract of *Schistosoma mansoni*". Mem. Inst. Oswaldo Cruz. 77(3): 275-283).

The U.S. Pat. No. 4,396,600 issued on Aug. 2, 1983 in the name of Luigi Messineo & Mauro Scarpin described an extract of adult Schistosome *mansoni* worms obtained by incubation in 0.15M sodium chloride-sodium phosphate buffer pH 5.8. The extract contains protein, carbohydrates, and nucleic acid and or by-products of the latter component and resolves into four major fractions (I-IV) by gel chromatography in G-100 and G-200 Sephadex columns. Immunodiffusion tests with rabbit anti-total extract serum reveal three precipitation lines corresponding to fractions I and II and one with III or IV. Rabbits immunized with this total extract are found to be totally or partially (at least 77%) resistant to a challenge infection. The saline extract antigenic material is an effective vaccine for the treatment and immunization of schistosomiasis and other schistosome infections.

Another published study is "A 14-KDa *Schistosoma mansoni* Polypeptide is Homologous to a gene family of fatty Acid Binding Proteins—The Journal of Biological Chemistry—vol. 266, No. 13, Issue of May 5, pp. 8447-8454, 1991; D. Moser, M. Tendler, G. Griffiths, and Mo-Quen Klinkert". This study describes the sequencing of the gene and the demonstration of the functional activity of Sm-14 as a protein which binds lipids.

Thus, schistosome antigens present in SE and other related helminth antigens have been cloned, sequenced, characterized, and the corresponding recombinant proteins prepared. Examples are: Sm14 (U.S. Pat. No. 5,730,984 granted to Fundação Oswaldo Cruz on 24 Mar. 1998; Fh-15 (Perez et al. (1992). "*Fasciola hepatica*: Molecular cloning. Nucleotide sequence and expression of gene encoding a polypeptide homologous to a *Schistosoma mansoni* Fatty Acid-Binding Protein". J. Exp. Parasitol. 74(4): 400-407.

However, vaccines which are based on the use of proteins belonging to the pathogen, be they altered or not, are not always easily obtainable. Difficulties in the extraction, purification, quantitative analysis and modification of such proteins are common problems with this type of vaccine. Solutions exist for some such cases but these may result in an additional onus to the protein production process which goes against the general principle that a vaccine should be of relatively low cost and should be globally accessible.

As an alternative, although not without its own deficiencies, is the use of synthetic peptides as vaccines.

There were attempts to combine epitopic portions of more than one antigen to raise their immunological properties. An example of this approach is described in the U.S. Pat. No. 5,219,566 granted to The John Hopkins University on 15 Jun. 1993 and refers to the construction of polypeptides based on the identification of epitopic regions which are common to two *S. mansoni* proteins. The polypeptides have epitopes which are shared by the 200 and 38 kDa proteins of *S. mansoni* and are able to bind to protein epitopes but not glycan epitopes expressed on the surface of live schistosomula of *S. mansoni*. The epitope (or epitopes) on the 38 kDa protein are exposed to the surface of the schistosomula while the epitope on the 200 kDa protein is apparently not exposed to the surface of schistosomula. A fusion protein having portions of any bacterial protein which is well expressed, particularly using portions of the amino terminal end of the enzyme beta-galactosidase, is included in the invention. It is mentioned that the particular subset of adult worm antigens was selected based on its enhanced reactivity with sera of vaccinated as compared to chronically infected mice.

Although many antigens from helminths are available and have been studied in connection with their protective potential only six *Schistosoma mansoni* antigens were selected by the WHO (World Health Organization) as vaccine candidates against diseases caused by schistosomes (see Progress Report 1975-94, Highlights 1993-94—20 Years of Progress, Tropical Disease Research WHO, Geneva, 1995). The selected antigens are: GST-28 kDa (also known as Sh28-GST)—a Glutathione S-Transferase, which is located in the schistosomula or adult worm parenchyma and in the adult worm backbone; Paramyosin-97 kDa—a muscle protein from adult worms or schistosomula; Sm23-23 kDa—a membrane protein from adult worms; IrV5-62 kDa—a protein which is homologous to myosin and is present in all parasite stages; TPI-28 kDa—a Triose Phosphate Isomerase and rSm14-14 kDa—from adult worms and belonging to the Fatty Acid-Binding Protein family.

Of these six vaccine candidates against *S. mansoni* initially selected by the WHO, four have been subsequently endorsed for scale-up to GMP grade antigen production and phase I/II clinical trials in humans. Two of these, Sh28-GST and Sm14 are closest to reaching this reality with GST already in phase II clinical trials for *S. haematobium* in Senegal and Sm14 in the final stages of scale-up. Furthermore, Sm14 is the only vaccine candidate to have been shown to afford significant immune protection against two relevant helminthic diseases of human and veterinary importance, namely Schistosomiasis and Fascioliasis.

Sm14 is thus a unique opportunity for attacking both the second most prevalent parasitic disease in humans—Schistosomiasis—and the most important helminth infection of cattle—Fascioliasis and therefore represents an attractive strategy for helminth vaccine development.

However, while some success has been achieved, these molecules are quite large.

A method currently under intensive investigation is the use of synthetic peptides corresponding to segments of the proteins from the pathogenic organism against which an immune response is directed. When these peptides are capable of eliciting a neutralizing immune response they appear to be ideal immunogens. They elicit a specific response and typically do not lead to deleterious effects on the host. However, it can be difficult to predict which peptide fragments will be immunogenic and lead to the development of a neutralizing response. It could be desirable to develop immunogens that elicit a response to specific neutralizing epitopes without causing responses to extraneous epitopes that could "dilute" the specific response or lead to harmful immune complex formation, including autoimmune reactions.

Such a method is accomplished by the identification of specific and discrete portions of proteins involved in the protein-protein interactions relevant to the immune response and the construction of biologically active peptides based upon the amino acid sequences identified.

Protein binding or protein-protein interactions can be broadly defined as an example of molecular recognition in which the surfaces of two macromolecules (proteins) or a peptide and a protein present discrete surface interactions involving chemical and shape complementarity. Such discrete interactions arise when residues of one protein (or peptide) are located spacially close to residues of another protein and attractive forces between the residues such as Van der Waals forces, salt bridges, hydrogen bonds, and hydrophobic interactions exist. The three-dimensional disposition of specific kinds of residues allows attachment to occur as a consequence of a large number of the above-mentioned weak interactions which together lead to a significant binding energy between the different proteins.

The hypervariable loops that occur in the complementarity determining regions of antibodies for example, on interacting with antigen epitopes may employ the wide range of chemical interactions described above. The binding surface or cavity on the antibody (paratope) is formed by the spacial distribution of the residues which comprise the variable domain of the antibody's light and heavy chains and particularly the hypervariable regions responsible for antigen complimentarily. Good fit of the antigen's epitope into the antibody's paratope depends on the shape and chemical nature of both components. The affinity of a given antibody for its antigen depends on the sum of the attractive and repulsive forces between epitope and paratope. However, since an antibody possesses two paratopes and given that many antigens are multivalent in nature, the overall antibody avidity will depend on the total number of paratopes and epitopes involved in the interaction.

A wide variety of topographies are observed for antibody combining sites. They may be relatively flat surfaces (common in the case of protein antigens), grooves (as is often the case for peptides) or cavities (in the case of small molecule haptens). Often exposed, flexible and highly protruding parts of a protein antigen (often corresponding to surface loops on the structure), are the immunodominant epitopes and there is evidence to suggest that there is flexibility in both the antigen and antibody which is necessary for an optimal 'induced' fit on complex formation.

Similarly for other types of molecular recognition important in the immune response, individual structural elements of the proteins involved are fundamental for the specificity. This is true for example in HLA interactions with processed peptides and in the interaction of the T-cell receptor with such HLA-peptide complexes.

By identifying the specific and discrete portions which confer antigenic properties to a particular protein, biologically active peptides can be constructed to mimic pathogen antigens and act on mammalian cells by binding to the receptor sites of those cells to alter or affect their function or behavior, or to prevent or alter the effect which pathogen antigens would otherwise have upon those cells. Such mimicking molecules would be useful as agents to affect the cells in the same manner as the natural protein. Alternatively such peptides may bind to soluble antibody.

As such, active peptides derived in this manner may elicit either T-lymphocyte and/or B-lymphocyte immune responses. Accordingly, the document WO91/09621 discloses a peptide fragment bearing amino acid sequences of the 28 kDa *Schistosoma mansoni* antigen which shares at least one epitope which induces a T-lymphocytes specific response and at least one epitope which induces a B-lymphocytes specific response. The peptide fragment described in that patent application corresponds to $2^n$-fold the amino acids 115-131 of the 28 kDa *Schistosoma mansoni* protein. It is mentioned that the advantage in using such a peptide fragment is to induce both humoral and cellular responses while the original protein (28 kDa of *S. mansoni*) does not induce almost any humoral response. It is also mentioned that the peptide fragment confers a protection of about 40-50% in animal models (rats).

EP 251 933 proposes a process for isolating a peptide fragment bearing at least one epitope of the 28 kDa of *S. mansoni* by subjecting, under controlled proteolytic conditions, the 28 kDa polypeptide of *S. mansoni* to the action of the protease V8. The applicant mentions that the preferred peptide fragments are those of 8 kDa and of 6 kDa which bear the anti-*Schistosoma* antigenic activity shown by the 28 kDa protein. The amino acid sequences of the peptide fragments were not disclosed in the patent application.

Synthetic vaccines which comprise a peptide fragment of sufficient size are considered to be of critical importance in providing the active portion or portions of the entire antigen which can be recognized by the immune system and evoke formation of the corresponding antibodies. Biologically active peptides can be constructed which function as the epitope or mimic a biologically active protein. Alternatively, biologically active peptides can be constructed which interact with receptors and thereby block the binding of a pathogen antigen or biologically active protein to a receptor.

U.S. Pat. No. 5,019,383 describes a synthetic vaccine comprising a peptide residue coupled to one or more alkyl or alkenyl groups of at least 12 carbon atoms in length or other lipophylic substance. It is described that the peptide residue contains a sequence of 6 amino acids corresponding to the sequence of such amino acids in a protein antigen or allergen where the greatest local average hydrophilicity of the antigen or allergen is found. Moreover, it is mentioned that the alkyl or alkenyl groups are the carrier on which the peptide residue is disposed, said carrier being of critical importance in providing the active portion of the synthetic peptide chain with sufficient size so that the entire synthetic antigen or synthetic allergen can be recognized by the immune system and evoke formation of the corresponding antibodies. It is also described that the synthetic peptide residue has a chain length of minimally six amino acids, preferably twelve amino acids and can contain an infinitely long chain of amino acids or their components, which can be characterized by the presence of other epitopes of the same or different antigen or allergen.

Another example of an active peptides approach is disclosed in the patent application WO93/23542 which refers to nucleic acid molecules containing nucleotide sequences encoding helminth aminopeptidase enzymes, and antigenic fragments and functionally-equivalent variants thereof, their use in the preparation of vaccines for use against helminth parasites, and synthetic polypeptides encoded by them. The invention of WO93/23542 is based upon the role of mammalian integral membrane aminopeptidases in cleaving the small peptides which are the final products of digestion.

In short, the identification of epitopic regions of pathogen antigens or biologically active proteins can be used in the construction of biologically active compounds which comprise equivalent or shared amino acid sequences. Furthermore, biologically active compounds, such as peptides, can be modelled based upon amino acid sequences of biologically active proteins whose epitopic regions are known.

However, peptides are basically fragments of polypeptide chain of limited size, which may be sometimes modified with respect to the original sequence of amino acids as found in the parent protein from which the fragment is derived. This presents a series of problems. Factors such as peptide solubility, degradation, aggregation, conformational stability, among others, are relevant given the final objective intended for the peptide.

As discussed above, Sm14 is a protein of particular interest. It is a cross reactive antigen which confers protection against both schistosomiasis and fasciolosis (see Tendler, M. et al. (1996). "A *Schistosoma mansoni* fatty acid binding protein, Sm14, is the potential basis of a dual-purpose anti-helminth vaccine". Proc. Natl. Acad. Sci. 93: 269-273 and U.S. Pat. No. 5,730,984). The data presented in these publications show the effectiveness of Sm14 in conferring high levels of protection against helminth infections.

Thus, the antigen Sm14 is an especially suitable active protein which can be used to model biologically active peptides based upon the determination of its cross-reactive epitopes.

SUMMARY OF THE INVENTION

The present invention relates to peptide fragments which have one or more shared and/or similar amino acid sequences to amino acid sequences of specific portions of the 14 kDa protein of S. mansoni, Sm14, or related FABPs, the said peptide fragments functioning as the continuous or discontinuous epitopic regions of Sm14

It is an object of the invention to prepare active peptides having identical or appropriately substituted amino acid sequences to those of amino acid sequences of one or more epitopic regions of the Sm14 antigen or related FABPs.

It is another object of the present invention to provide a process for constructing active peptides which mimic the Sm14 antigen or related FABPs or prevent the interaction between helminth pathogens and receptors.

It is yet another object of the present invention to provide an immunogenic compositions able to confer at least partial protection against infection with pathogenic helminths, and thus serve as vaccines against same.

It is still another object of the present invention to provide a diagnostic test for helminth infection diagnostics using active peptides having similar or appropriately modified amino acid sequences to those found in epitopic portions of the Sm14 antigen or related FABPs.

BRIEF DESCRIPTION OF THE DRAWINGS

FIG. 1 illustrates the sequence alignment of members of the FABP family used for comparison of Sm14 and Fh15 with other FABPs.

FIG. 3 shows sequence alignment of FABPs highlighting β-sheets (light gray indicates β-sheets and dark gray indicates β-budges) and the position of Sm14 residues which suggest immunogenic relevance (# indicates residues which are solvent accessible, these residues being located at the following positions: 1, 18, 22, 26, 41, 43, 48, 63, 66, 86, 88, 89, 90, 93, 99, 106, 109, 111, 119, 120, 121 and 122; $ indicates the residues that are not solvent accessible, said residues being located at the following positions: 42, 49, 80, 94, 114, 125). These are identical to those indicated in FIG. 1.

FIG. 10 shows the representation of secondary structure elements of Sm14 which was the template to model the peptides of the invention. Unshaded residues indicate connections between elements of secondary structure; ($) indicates solvent-inaccessible residues of epitopes; (#) indicate solvent-accessible residues of epitopes. The peptides of the invention can be ready located with reference to Tables 1 and 2.

FIG. 14 illustrates parasite FABPs. Alignment showing secondary structure elements of Sm14 and its residues which have a relevant role in eliciting immunogenic response (# indicates solvent accessible residues and $ indicates the residues that are solvent inaccessible).

DETAILED DESCRIPTION OF THE INVENTION

For convenience, the meaning of certain terms and phrases employed in the specification, examples, and appended claims are provided below.

The term "active protein" refers to proteins which bind to cellular receptors and thereby alter or affect the function or behavior of the cells, or prevent or alter the effect which another biologically active protein would otherwise have upon those cells. A pathogen antigen can be a biologically active protein if, upon binding to a host cell, it alters or affects the function or activity of a cell or prevents another agent from doing so.

As used herein the term "neutralizing epitope" refers to the portion of a pathogen antigen against which antibodies have a neutralizing activity. That is, antibodies specific for a neutralizing epitope render the pathogen non-infective and/or inactive.

The term "receptor site" refers to the portion of the receptor that interacts with a protein that binds to the receptor.

The term "active peptides" refer to proteinaceous molecules which mimic biologically active proteins or prevent the interaction between biologically active proteins and receptors, where receptors may be molecules of the immune system including antibodies.

The terms "correspond" and "corresponding" refer to the level of shared identity between two amino acid sequences and the terms "homologous", "homology", and "sequence similarity" are often used interchangeably by those having ordinary skill in the art to refer to related amino acid sequences.

It has been amply discussed here that the state of the art teaches that it has been verified that the Sm14 protein offers protection in animal models (Swiss mice and New Zealand rabbits) which have been infected with *Schistosoma mansoni* and previously stimulated with Sm14. Furthermore, parallel experiments in which animal models were infected with *Fasciola hepatica*, causative agents of Fasciolose, after previously being stimulated with Sm14, also demonstrated the existence of a protective cross reactivity.

Figure 1:
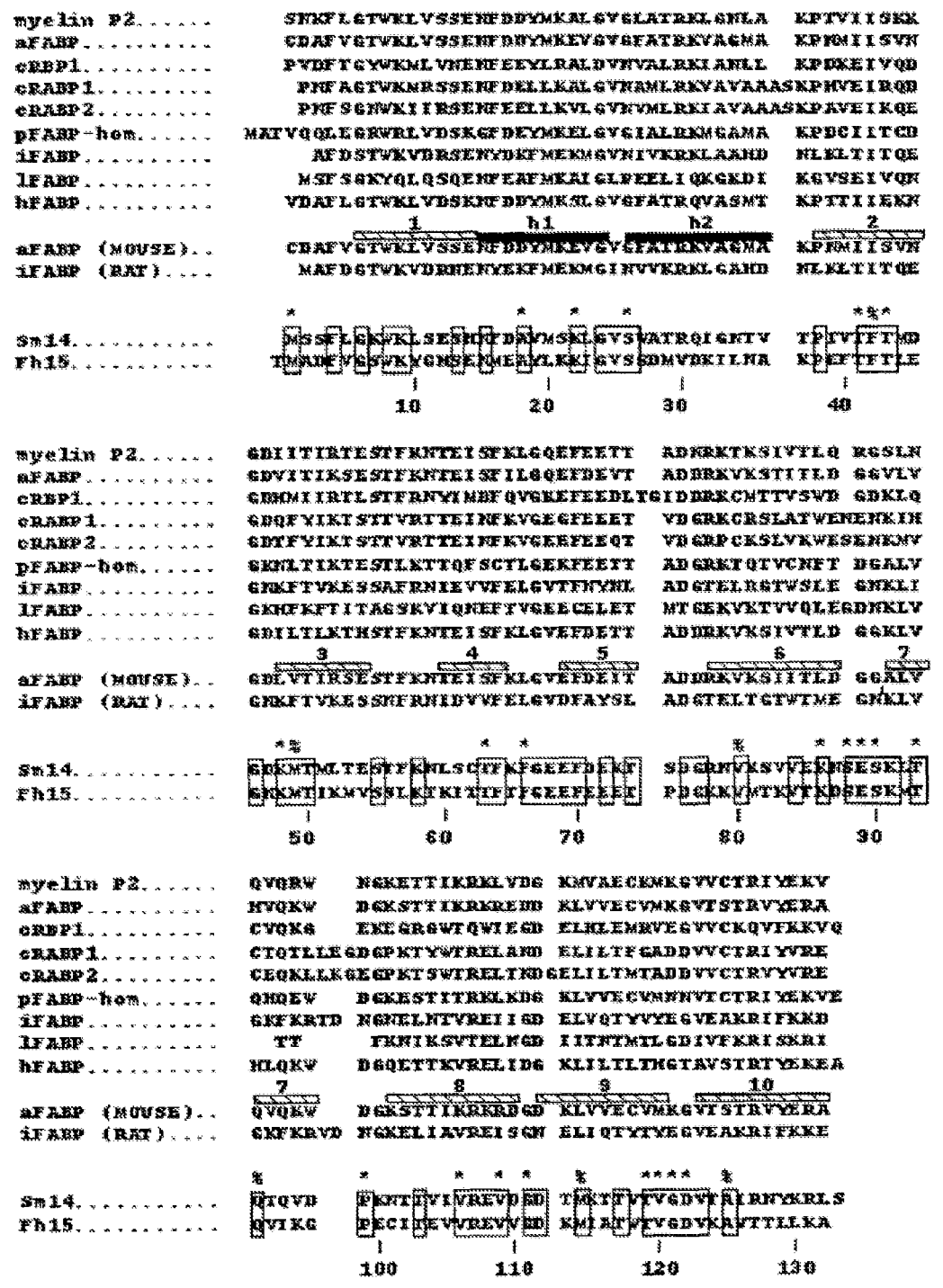
Figure 2A:
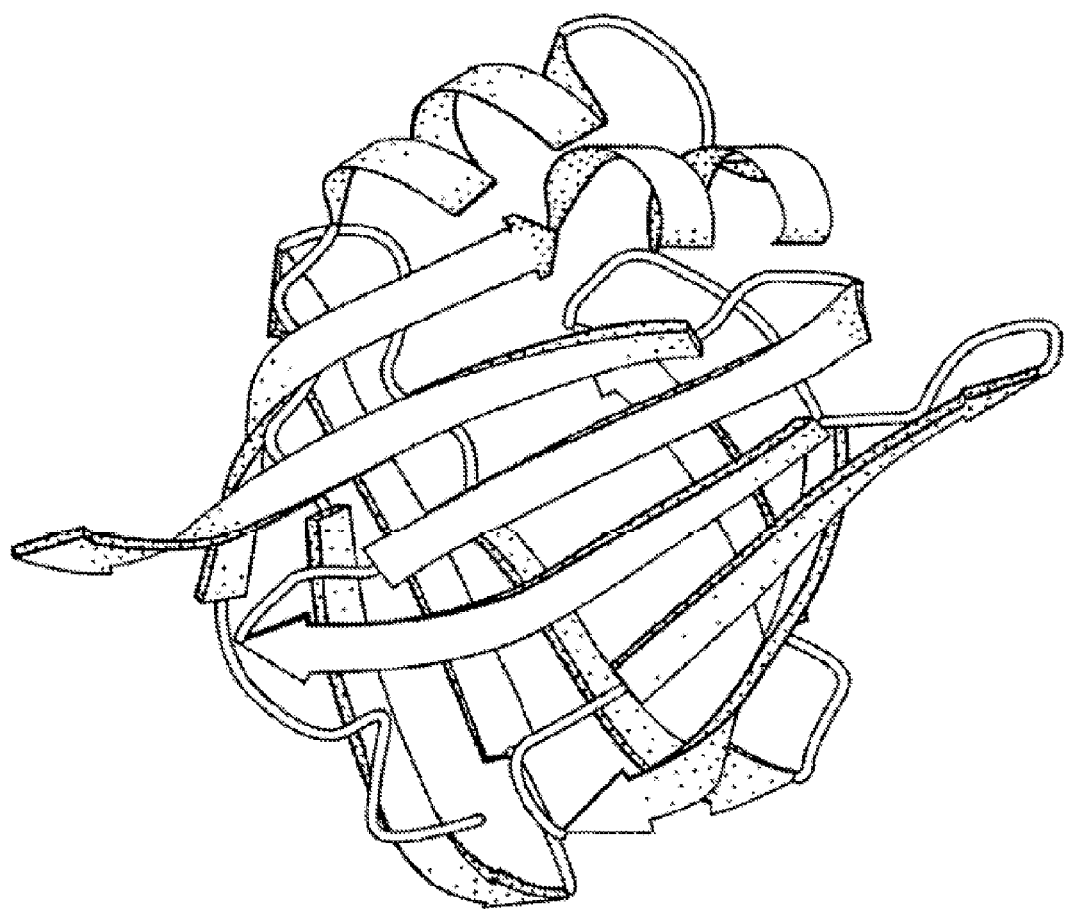
FIG. 2A schematically illustrates the basic architecture of FABPs.

Sm14 belongs to the intracellular Fatty Acid-Binding Protein family—the FABPs, whose amino acid sequence is shown in FIG. 1 and whose three-dimensional structure can be schematically represented as shown in FIG. 2A.

Fh15, from *Fasciola hepatica* also belongs to the intracellular Fatty Acid-Binding Protein family. Its amino acid sequence is also given in FIG. 1 and it is also schematically represented in FIG. 2A.

FIG. 1 also shows the amino acid sequences of a series of host (human) FABPs. From the figure it can be verified that Sm14 and Fh15 show a degree of sequence identity which is of a similar order to that observed between Sm14 and many of the remaining (host) FABPs. This is of the order of 35 to 40%.

Specifically, in FIG. 1 the first nine sequences are all of proteins derived from human tissues: myelin P2 from peripheral nerve; adipocyte FABP, aFABP; cellular retinol-binding protein I, cRBPI; cellular retinoic acid-binding proteins I and II, cRABP1 and cRABP2; psoriasis-related FABP homologue, pFABP-hom; intestinal FABP, iFABP; liver FABP, lFABP; and heart FABP, hFABP. FABPs from mouse adipocyte and rat intestine are also shown, as they were used together with hFABP for the construction of molecular models for Sm14 and Fh15 (Tendler, M. et al. (1996). "A *Schistosoma mansoni* fatty acid binding protein, Sm14, is the potential basis of a dual-purpose anti-helminth vaccine". Proc. Natl. Acad. Sci. 93: 269-273). The β-sheet strands of a FABP are indicated by the hatched blocks and numbered consecutively; the two α-helices (h1 and h2) are marked by the solid bars. Identical residues in the two parasite sequences (Sm14 and Fh15) are boxed. The subset of these residues which are conserved in no more than three of the human sequences are indicated either by stars (for exposed residues) or by the percent symbol (for solvent inaccessible residues).

Figure 3:
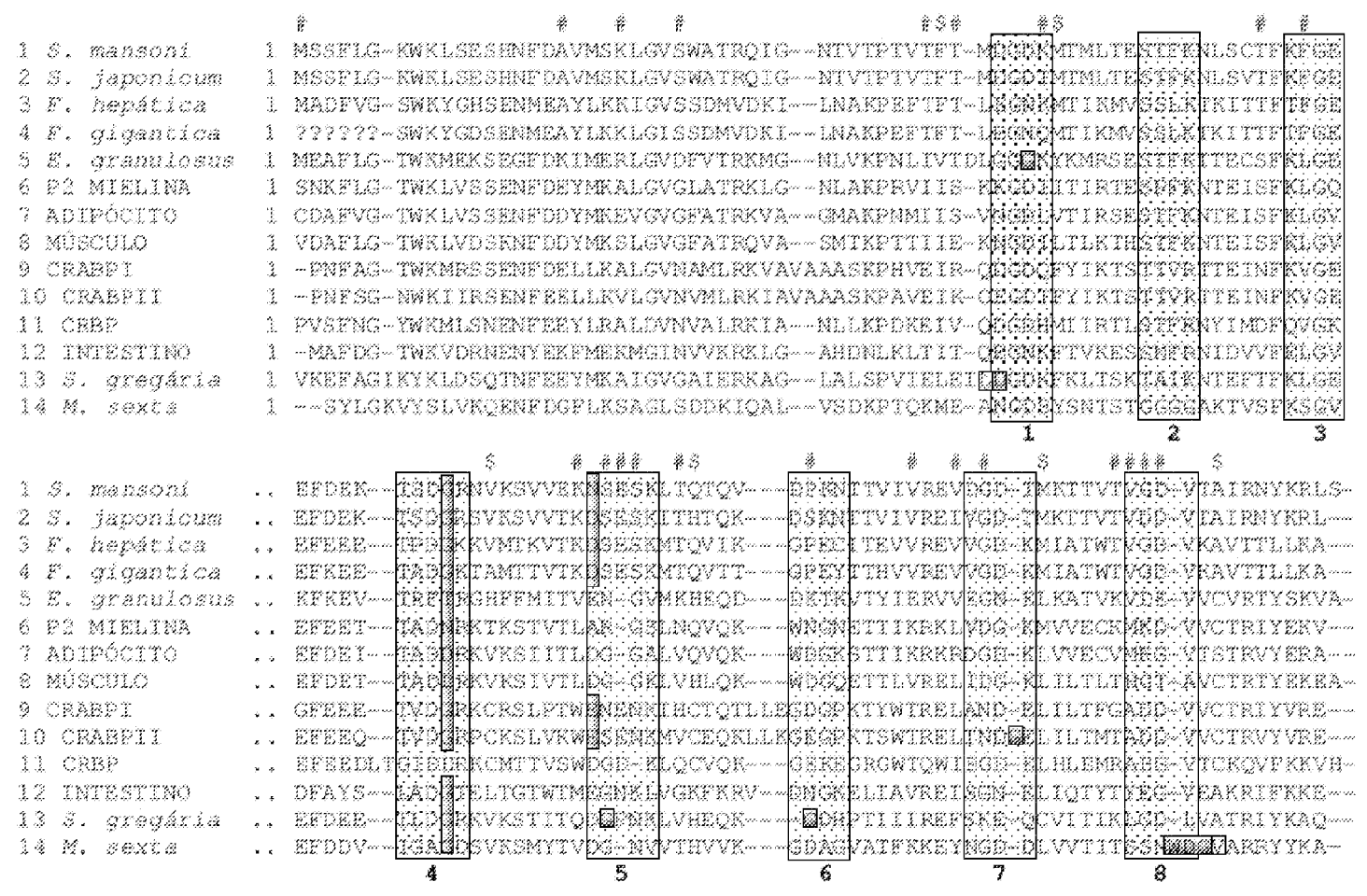

As can be seen from FIG. 1 the alignment of the host and parasite (Sm14 and Fh15) FABPs together with two sequences of known three-dimensional structure (aFABP and iFABP) permits the definition of regions which are structurally equivalent. These were used in the construction of the model of Sm14 and Fh15 described in Tendler, M. et al. (1996). "A *Schistosoma mansoni* fatty acid binding protein, Sm14, is the potential basis of a dual-purpose anti-helminth vaccine". Proc. Natl. Acad. Sci. 93: 269-273 and have also been used in the construction of models for FABPs from *Schistosoma japonicum* (Sj14), *Fasciola gigantica* (Fg15) e *Echinoccocus granulosus* (Eg15) based on the alignment shown in FIG. 3.

Sm14 is as closely related to several human proteins, including P2 myelin protein (≅42% sequence identity) and FABP from cardiac muscle ((≅42%), as it is to Fh15 (≅44%), which is a FABP from *Fasciola hepatica*. However there is good evidence for immune cross-reactivity between the two parasite proteins, whilst there are no reports of *S. mansoni* patients developing auto-imune reactions. It is of interest therefore to determine the specific characteristics of these two parasite FABPs, in terms of regions of amino acid sequence and structure, which are responsible for such cross-reactivity.

Figure 4:
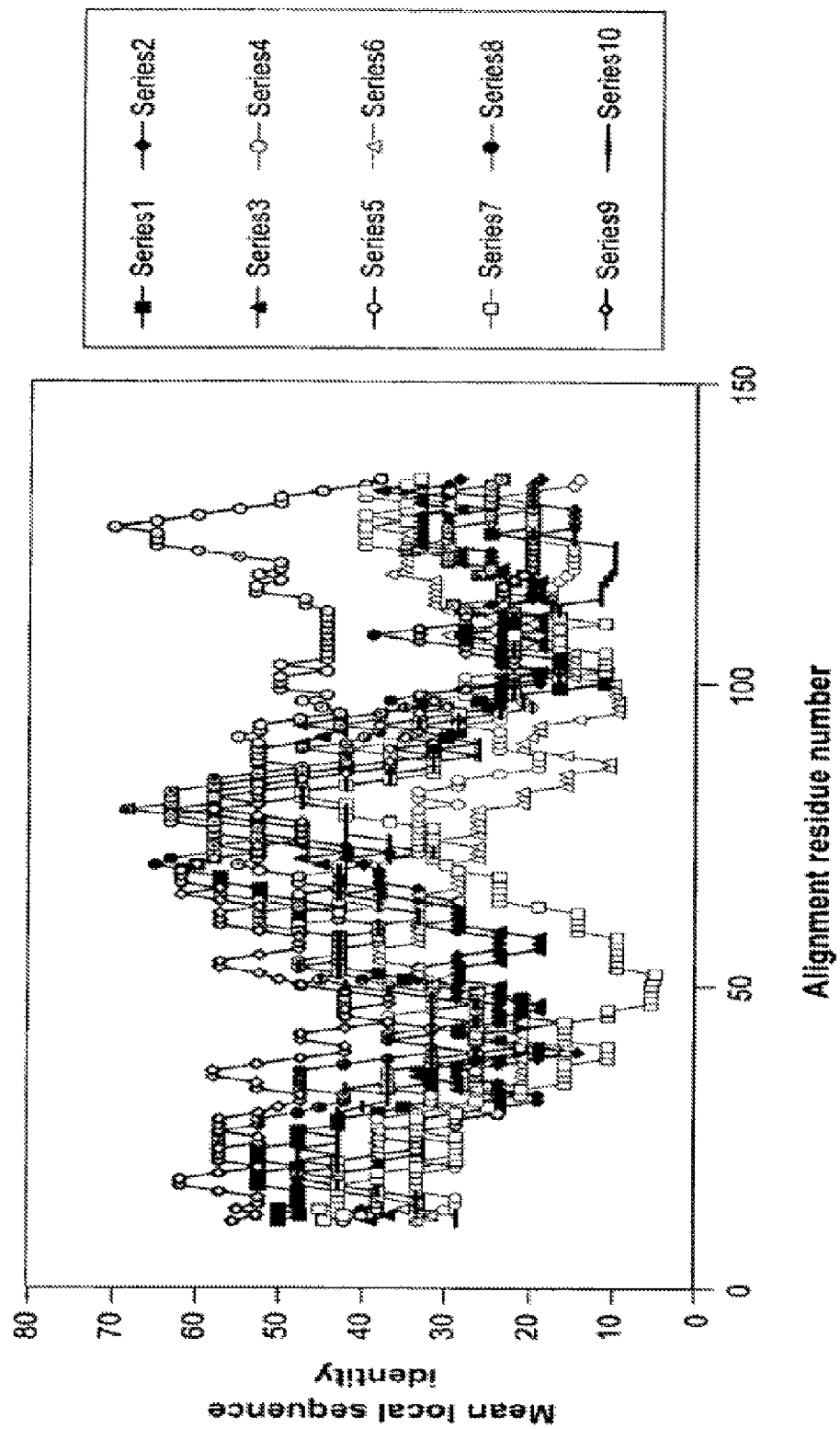
FIG. 4 shows local sequence identity in pairwise comparisons between human and parasite fatty-acid binding proteins. Sequence identity is calculated within a sliding window of 21 residues and plotted as a function of the central residue for comparisons of Sm14 with human adipocyte FABP (series 1), cellular retinoic acid binding protein I (series 2), cellular retinoic acid binding protein II (series 3), cellular retinol binding protein I (series 4), Fh15 (series 5), intestinal FABP (series 6) liver FABP (series 7), muscle FABP (series 8), P2 myelin protein (series 9) and psoriasis-related FABP homologue (series 10). Towards the C-terminus (after alignment position 90) the curve corresponding to the comparison between Sm14 and Fh15 is clearly distinguishable from the remainder.

Despite this observation the Sm14 and Fh15 molecules do not exhibit simple, coordinated alterations in size or continuous sequence when compared with their human homologues. However Sm14 does show a marked falloff in conservation with human sequences towards the C terminus (from about residue 85 onward) whereas the two parasite sequences show approximately 47% mean identity within the same region. In general this is the most poorly conserved region of the molecule across the family of FABPs as a whole (Jones et al. (1988) EMBO J. 7, 1597-1604; Sacchettini J. C. et al. (1988) J. Biol. Chem. 263, 5815-5819; Muller-Fahrow, A. et al. (1991) Eur. J. Biochem. 199, 271-276)). There is thus a notable difference between the parasite proteins and their human homologues in that the C-terminal region of the former shows an unusual level of sequence conservation. This is shown in FIG. 4 where the average mean conservation within a 21 residue sliding window is calculated as a function of sequence position for pairwise comparisons which involve Sm14 and one other FABP. Only in the case of the comparison between Sm14 and Fh15 is a clear peak in the graph seen towards the C-terminus. The β-strands of this region (from residue 85 onwards) are shown in a lighter shade of grey in FIG. 2B in order to distinguish them from the remainder of the molecule. Indeed the cross-reactivity of these two proteins has already been demonstrated experimentally (see Perez et al (1992) and Tendler et al (1996).

We (Tendler, M. et al. (1996). "A *Schistosoma mansoni* fatty acid binding protein, Sm14, is the potential basis of a dual-purpose anti-helminth vaccine". Proc. Natl. Acad. Sci. 93: 269-273) have described molecular models constructed for both Sm14 and Fh15 and shown that the two molecules adopt the same three-dimensional topology as other members of the FABP family. The basic architecture of FABPs is represented in the FIG. 2A.

Figure 2B:
FIG. 2B schematically illustrates the ribbon diagram of the molecular model for Sm14 constructed on the basis of the three-dimensional structures of the homologous molecules from mouse adipocyte, rat intestine, and human muscle. The β-sheet strands in the C-terminal region of the molecule (from residue 85 onward) are shown in a lighter shade of grey. Residues shown in ball-and-stick representation are identical in both Sm14 and Fh15 and are solvent exposed. The Figure was produced with the program RIBBONS (see Carson, M. (1987). J. Mol. Graphics. 5: 103-106).

As showed in FIG. 2B, the molecular model of Sm14 consists of a 10-stranded antiparallel β-barrel with short interstrand connections which generally form reverse turns (β-turns). Strands 7-10 of the barrel with their connections loops essentially constitute the C-terminal portion of the molecule. When residues conserved (i.e. identical) in Sm14 and Fh15 but present in no more than three of nine human sequences were plotted on the modeled 3D structure, two probable epitopes were identified and selected for purpose of the present invention. These are discontinuous as they are constituted by residues which are spacially close in the three-dimensional structure but distant in the amino acid sequence. Twenty-two of these residues were exposed on the surface and thus potentially contribute to B-cell mediated antigenicity. Of these 22 residues, 13 were derived from the C-terminal portion of the protein, which we show to present an unusually high degree of conservation. The external invariant residues are not randomly distributed about the surface of the Sm14 molecule but rather are clustered at the upper and lower ends of the barrel (FIG. 2B) and potentially constitute functional discontinuous epitopes which present significant variation from human proteins. The clustering of 13 of the 22 conserved exposed residues within the C-terminal region, together with the evidence from FIG. 4 indicates the importance of the C-terminal region (together with residues from other parts of the molecule which come together to form discontinuous epitopes), for antigenicity. Indeed, the four interstrand connections which are included within the C-terminal part of the structure show pronounced peaks in the main-chain accessibility, a phenomenon often correlated with antigenic determinants.

In the current invention we describe a method for the unification of two distinct peptides derived from the Sm14 molecule, which are distant in primary structure (amino acid sequence) but spatially close in tertiary structure. Said peptides belong to the same predicted discontinuous epitope. Besides simply unifying the peptides into a single larger peptide, the current invention also describes a method for modifying the amino acid sequence of said peptides such that the resulting peptide adopts a three-dimensional structure which is similar to the corresponding regions of the parent (Sm14) molecule or that such a structure may be energetically accessible to the peptide in solution or that such a structure may be acquired by the peptide on complex formation with molecules of the immune system, such as antibodies. This approach is applicable to other protein antigens which present discontinuous epitopes.

According to the present invention the method for constructing peptides on the basis of the three-dimensional structures of homologous molecules wherein said peptides are able to mimic or prevent the interaction between helminth pathogens and receptors, said method consisting of:

(i) selecting regions of the parent protein which contain a high spatial density of residues which form continuous or discontinuous epitopes;

(ii) give priority to maintaining the previously predicted epitopic residues, responsible for stimulating the desired immuno/antigenic response, within the selected peptide sequence;

(iii) elaborate sequences which, whilst maintaining a high percentage of previously identified epitopic residues, are of limited size varying from 8 to 28 residues;

(iv) two peptides may be chosen, which may correspond to regions which are distant in the primary structure (amino acid sequence) but spatially close in the tertiary (three-dimensional) structure, the said regions are chosen on the basis that the three-dimensional structure indicates that they can be readily united assuming that they retain their original structures.

(v) modifications may be made to the peptide, be it derived from a single continuous stretch of amino acids or be it derived in the manner described in (iv), so as to favour the three-dimensional conformation as seen in the original protein, such modifications may include substitutions of amino acids as well as insertions or deletions of amino acids;

(vi) residues, such as ½-cystines, may be used in order to restrict the conformational freedom of the final peptide.

In step (iv) a minimal requirement is that the C-terminus of one peptide should be spatially close to the N-terminus of the second peptide, but there is no need to necessarily preserve the order of the peptides as exists in the original protein.

Amino acid sequence determination can be readily accomplished by those having ordinary skill in the art using well known techniques. Generally, DNA sequencing of relevant genetic material can be performed and the amino acid sequence can be inferred from that information. Sequencing of genetic material, including cDNA, can be performed by routine methods by those having ordinary skill in the art and thus can readily determine whether or not one amino acid sequence corresponds to another. The determination of whether sequences are corresponding may be based on a comparison of amino acid or nucleic acid sequence, and/or protein structure, between the proteins of interest. In the case relevant to the current invention, the determination of the amino acid sequence of the pathogen antigen (Sm14) shows it to correspond to (be homologous to) members of a family of Fatty Acid-Binding Proteins (FABPs).

By determining the number of identical and conservatively substituted amino acid residues shared between two molecules once aligned by standard techniques, and knowing the length of the alignment, one having ordinary skill in the art can determine whether or not two sequences correspond. Depending on the sequence length, the two sequences correspond (are homologous) if they share approximately at least 80% identical and conservatively substituted amino acids of which at least about 28% are identical amino acids and between about 30-42% conservative substitutions.

The peptide is synthesized and mimics the pathogen or biologically active protein. The peptide is formulated as a pharmaceutical composition which is administered, for example, as a therapeutic to elicit the activity that the native proteins have on cells.

The following examples are illustrative of the invention and represent preferred embodiments. Those skilled in the art may know of, or may be able to find using no more than routine experimentation, other appropriate materials and techniques such as the above mentioned amino acid sequences and production methods.

Example 1

Method for Obtaining the Peptide

The three-dimensional structure of Sm14, as built by comparative homology modeling and described in Tendler et al. (1996), was used as the basis for obtaining peptide fragments for synthesis and subsequent vaccination trials. It should be noted that in previous studies we described likely discontinuous epitopes responsible for the immune cross-reactivity between Sm14 and Fh15 and a summary of these results has been given above.

The residues predicted to participate in such epitopes were identified on the basis of the fact that they are identical in the two parasite molecules and yet only poorly conserved in human homologues. Due to the fact that few of the predicted epitopic residues were present in continuous stretches of the amino acid sequence, a design strategy was elaborated in order to incorporate more than one continuous segment into a single unified peptide.

In order to aid in obtaining segments of the polypeptide chain which were of greatest interest for incorporation into peptides for vaccination purposes, the local sequence conservation of parasite and host fatty acid binding proteins was first evaluated. This was done by calculating the local percentage sequence identity between any two sequences within a 21 residue-sliding window. Comparisons were made between Sm14 and Fh15 and between Sm14 and nine human fatty acid binding protein homologues.

FIG. 4 shows the results of the sequence comparisons made between nine human fatty acid binding proteins and Sm14. On calculation of sequence identity within a sliding window of 21 residues, it can be readily seen that in general the local similarity between Sm14 and human homologues falls off rapidly towards the C-terminus. This lack of sequence conservation in the C-terminal part of the molecule has been commented previously and is in direct contrast to the pattern observed when comparing the two parasite FABPs, Sm14 and Fh15, in which the C-terminal third of the molecule shows the greatest overall sequence conservation. Distinct patterns of residue conservation are thus apparent when comparing either the parasite derived Sm14 with its host's homologues or alternatively with the cross-reacting homologue from a related parasite. This is despite the fact that the overall percentage identity along the entire sequence may be very similar in both cases (42% on comparing Sm14 with human cardiac FABP or P2 myelin protein and 44% with Fh15).

This result suggests that judiciously chosen peptides carrying the epitopic residues predicted previously (Tendler, M. et al. (1996). "A *Schistosoma mansoni* fatty acid binding protein, Sm14, is the potential basis of a dual-purpose anti-helminth vaccine". Proc. Natl. Acad. Sci. 93: 269-273) and principally derived from the C-terminal region of the molecule, may be sufficiently distinct from human homologues to diminish the risk of undesirable cross-reactivity. At the same time, by choosing the peptides such that a reasonable number of residues conserved in Sm14 and Fh15 are included, it is desired to increase chances of the successful induction of a protective immune response against both parasites.

This is clearly an important factor when considering the use of such peptides as multivalent anti-helminthes vaccines.

On the basis of the above sequential analysis together with the predicted three-dimensional structure, two regions of the molecule were selected for peptide obtention with emphasis placed on the C-terminal third of the molecule. The first region is composed of two segments; an α-helix (located in the large connection between β-strands 1 and 2) together with the connection between β-strands 9 and 10. The peptides derived from this region of the molecule will be henceforth referred to as family number 1. The second region comes from the opposite side of the β-barrel which forms the basic structure of the molecule and is also discontinuous, in this case consisting of two β-hairpins. The first hairpin is composed of β-strands 6 and 7 and the second, β-strands 8 and 9, in both cases together with their connecting loops (type I and type II' β-turns respectively). The peptides derived from this region will be referred to as family 2.

For each family, the two individual segments chosen were selected on the basis of their spatial proximity in the three-dimensional structure and not on their proximity in terms of amino acid sequence. Furthermore in choosing the exact length of each component segment several additional criteria were taken into account. These included 1) an attempt to include a maximal number of the residues predicted in our previous studies to form part of the discontinuous epitopes, 2) an attempt to maintain the peptide as small as possible, 3) so as to facilitate the joining of the two segments into a single peptide with reference to the three-dimensional structure of the intact protein and 4) giving preference to segments which make a significant number of internal contacts.

Figure 5:
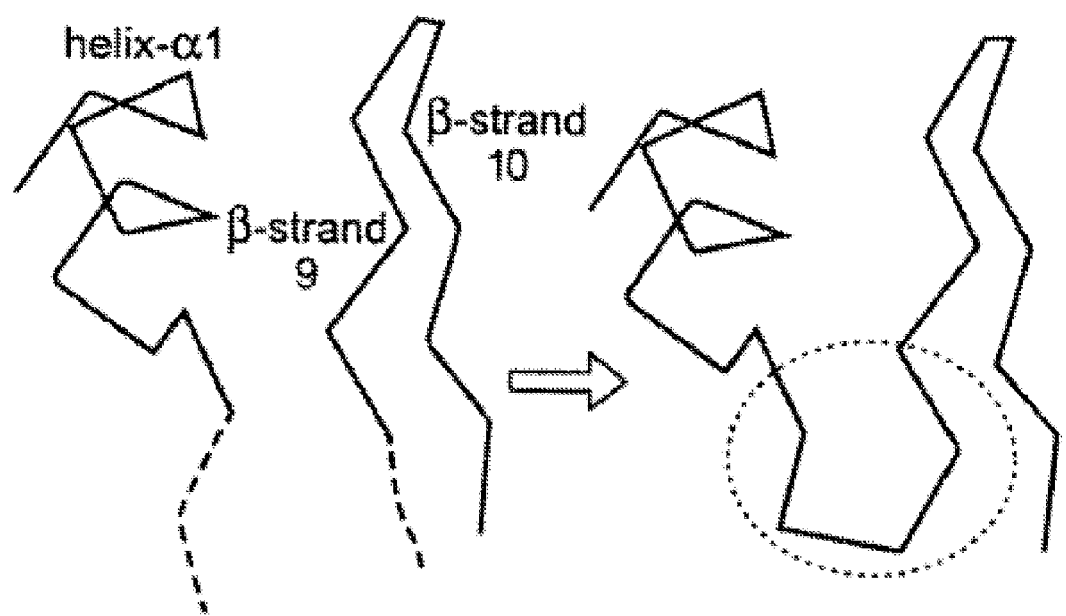
FIG. 5 illustrates schematically the formation of the fragments of the discontinuous epitope. As can be seen two regions which participate in a predicted discontinuous epitope are chosen to form components of a continuous synthetic peptide.

The third and fourth criteria were introduced in order that the two segments of a given family might be joined into a single peptide in such a way as to retain the possibility of maintaining the original structure as observed in the whole molecule and as illustrated in FIG. 5. This is by no means meant to imply that the peptide would naturally adopt such a structure in solution. Indeed this seems unlikely given the small size of the resulting peptides and the known conformational flexibility of such molecules in solution. Rather it is an attempt to ensure that such a conformation is energetically accessible, for example via induced fit on complex formation with antibody.

Figure 6:
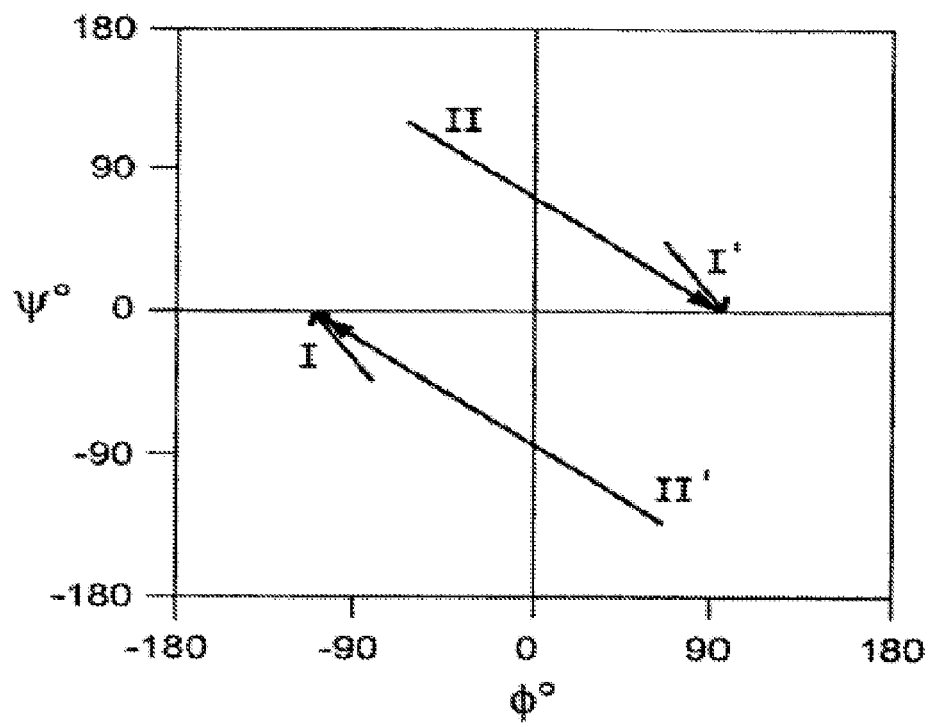
FIG. 6 provides general information about β-turns showing a graphic representation (Ramachandran plot) for preferred conformations of β-turn residues n+1 and n+2 located between β-sheets, for different turn types (I, II, I', II'). The preferences for different amino acid types at the four residue positions which participate in the β-turn have been established in previous art (for example Wilmot C. M. & Thornton J. M. (1988) "Analysis and Prediction of the different types of β-turn in proteins" J Mol Biol 203, 221-232).
Figure 7:
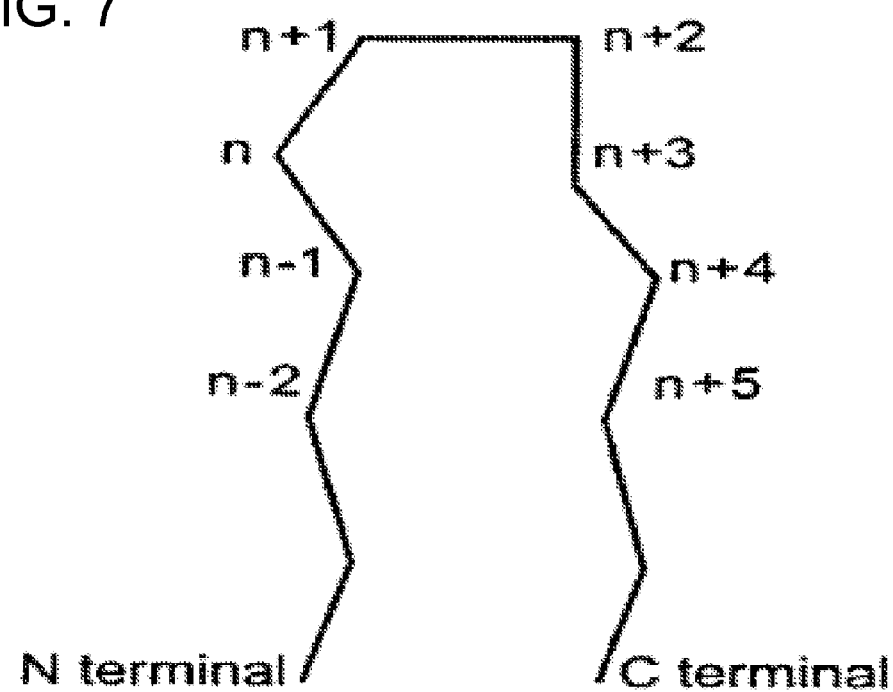
FIG. 7 is the nomenclature and composition of β-loop elements of FIG. 6.

The resulting fusion peptide, composed of the two component segments of a given family, was subsequently modified in an attempt to favor the native structure. Modifications were made based on the known frequencies of occurrence of amino acid residues in β-turns and using atomic contact quality analysis as implemented in the graphics program WHATIF (Vriend, G. (1990) J. Mol. Graph. 8, 52-56; Sibanda et al. (1985) Nature 316, 170-174). In the latter case, residues which became exposed to an unfavorable chemical environment as a result of being removed from the context of the entire structure were substituted, such that the peptide is no longer identical in amino acid sequence to that observed in Sm14 itself, but continues to correspond to it. Furthermore, this approach does not lead to the conclusion that such substitutions must be conservative in terms of the chemical nature of the amino acids involved. Indeed given that hydrophobic residues which are buried in the native structure will often be expected to become exposed in the peptide, it will often be necessary to make non-conservative substitutions and even deletions or insertions. Some information concerning β-turn types is given in FIGS. 6 and 7.

In the case of family 1, this resulted in four peptides. Peptide 1.1 was derived from the β-hairpin composed of strands 9 and 10, from residue 118 to 125. Peptide 1.2 was derived from the first α-helix of the structure, from residue 15 to 24. Peptide 1.3 was a direct fusion of 1.1 and 1.2, composed of 18 residues and 1.4 was derived from 1.3 by the substitution of four amino acid residues, based in the criteria described above.

Specifically, 1.4 has been modified in order to introduce two glycine residues at its centre aimed at favoring a bend in the peptide mainchain. Modeling studies indicated that glycines at this position assuming the conformation of a type I' turn would in principal be able to unite the two fragments whilst retaining their original structure as seen in the whole protein. Two further substitutions were made to hydrophobic residues of 1.3; the Phe at position 10 was replaced by a Ser and Leu at position 17 by Val. These residues are normally hidden within the hydrophobic core of the whole molecule and their substitution by less hydrophobic residues was guided by the WHATIF atomic contact quality option. After transforming 1.3 into 1.4, the quality score rose from 0.23 to 0.54 suggesting the substitutions to be reasonable, assuming the conformation expected for these regions in the Sm14 itself. This case exemplifies how the use of the three-dimensional structure of Sm14 for peptide modification, which is part of the current invention, is used in practice. It involves the use of substitution of the final residue of the first peptide (1.1) and the first residue of the second (1.2) by glycines in order to induce a reverse turn and also non-conservative substitutions.

In the case of family 2, six peptides were designed using a similar strategy. Peptide 2.1 (residues 85 to 94) came from the β-hairpin between strands 6 and 7. Likewise peptide 2.2 was derived from the hairpin between strands 8 and 9. Peptide 2.3 is a simple fusion of 2.1 and 2.2, whilst peptides 2.4 and 2.5 are alternative modifications thereof. In peptide 2.4 asparagine at position 3 of peptide 2.3 is substituted by phenylalanine, glutamine at position 10 by serine, an insertion of four residues (Asp-Pro-Thr-Gly) is made between Gln10 and Ile11, and residue Asp18 in peptide 2.3 is substituted by Ala22 in 2.4. In peptide 2.5 a smaller insertion of two residues is made between positions 10 and 11 of 2.3 together with the substitutions indicated in Table 2. In both cases the insertion of residues between the two fragments corresponding to 2.1 and 2.2 was made with the intention of uniting the fragments with β-turns. In the case of 2.4 the turn type intended was type I and in the case of 2.5, type I'.

According to the present invention alternative modifications in the original fragments are carried out when it is desired, for example in order to introduce conformational stability for the peptide.

Peptide 2.6 is identical in amino acid composition to 2.5 but its sequence has been randomized and was used as a control in immunization assays in order to evaluate the non-specific effect of a peptide of unrelated amino acid sequence but identical amino acid content.

Figure 8:
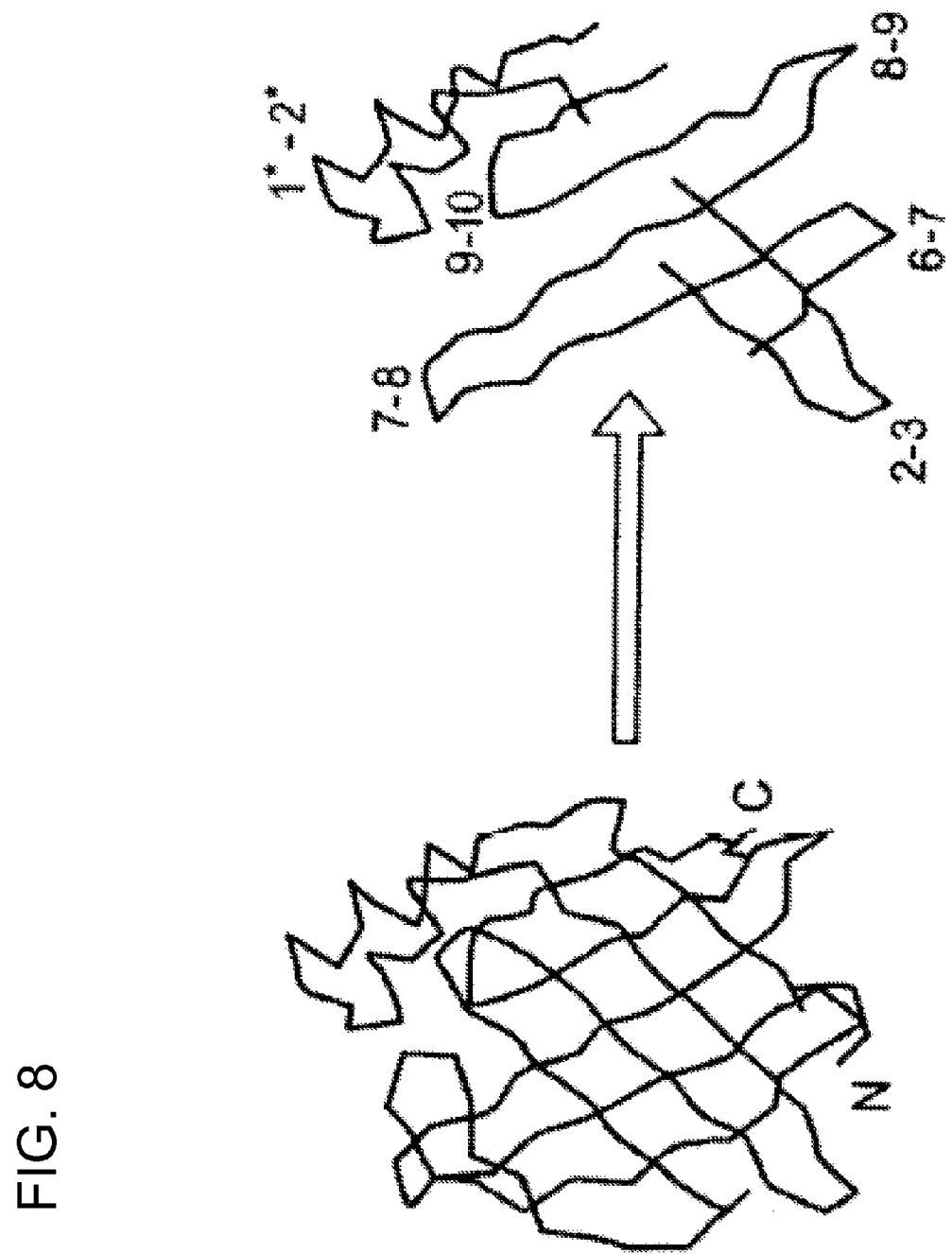
FIG. 8 schematically represents some of the regions from Sm14 which are of immuno/antigenic interest. The regions indicated 1*-2* (which comprises the connection between β-strands 1 and 2 and is composed of two α-helices) and 9-10, belong to family 1 as defined in the text. Those indicated 6-7 and 8-9 (being the connections between the corresponding β-strands) belong to family 2.
Figure 9:
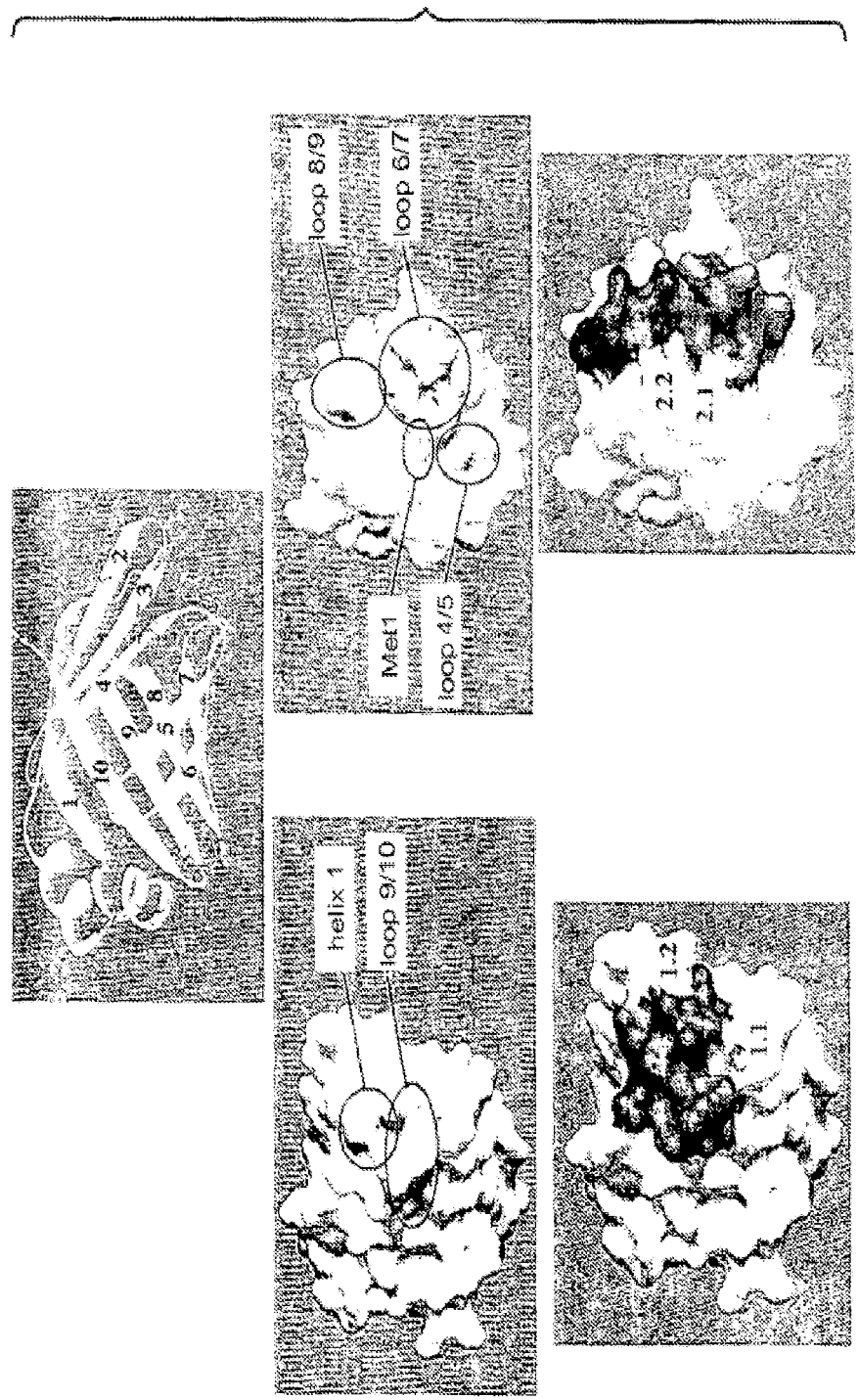
FIG. 9 shows the relationship between the three-dimensional structure of Sm14 and the peptides selected for vaccination trials. Specifically the regions of the molecular surface which correspond to the epitopic residues identified by Tendler et al. (1996) are shown (top center) as sticks. Center (left and right) show (in grey) how these residues map onto the molecular surface (in white). Single peptides and fusions of two peptides aim to represent the molecular surface corresponding to the epitopic residues as well as possible. The parts of the molecular surface corresponding to peptides 1.1 and 2.1 are shown in grey, and those corresponding to 1.2 and 2.2 in black (bottom left and right).

All of the final peptide sequences are given in Tables 1 and 2 and the four peptides which were directly derived from Sm14 (1.1, 1.2, 2.1 and 2.2) are shown schematically in FIG. 8 and mapped onto its model structure in FIG. 9. There sequences with respect to the original Sm14 amino acid sequence can be localized by referring to the following tables together with FIG. 10.

TABLE 1

Amino acid sequences of the peptides used in the immunization assays.
Family 1

| Peptide | Sequence | Comments |
|---------|----------|----------|
| 1.1 | VTVGDVTA (SEQ ID NO: 1) | Loop between β-strands 9 and 10 |
| 1.2 | NFDAVMSKLG (SEQ ID NO: 2) | (First α-helix between β-strands 1 and 2) |
| 1.3 | VTVGDVTANFDAVMSKLG (SEQ ID NO: 3) | Union of 1.1 and 1.2 |
| 1.4 | VTVGDVTGGSDAVMSKLG (SEQ ID NO: 4) | 1.3 modified |

TABLE 2

Amino acid sequences of the peptides used in the immunization assays.
Family 2

| Peptide | Sequence | Comments |
|---------|----------|----------|
| 2.1 | EKNSESKLTQ (SEQ ID NO: 5) | Loop between β-strands 6 and 7 |
| 2.2 | IVREVDGDTMKTT (SEQ ID NO: 6) | Loop between β-strands 8 and 9 |
| 2.3 | EKNSESKLTQIVREVDGDTMKTT (SEQ ID NO: 7) | Union of 2.1 and 2.2 |
| 2.4 | EKFSESKLTSDPTGIVREVDGATMKTT (SEQ ID NO: 8) | 2.3 modified |

TABLE 2-continued

Amino acid sequences of the peptides used in the immunization assays.
Family 2

| Peptide | Sequence | Comments |
|---|---|---|
| 2.5 | EKFSESKLTFDGIVREVDGATMKTT (SEQ ID NO: 9) | Alternate modification to 2.3 |
| 2.6 | KIGTSVFGTRTSKFDATEMVLDKEE (SEQ ID NO: 10) | 2.5 randomized |

FIG. 9 represents the relationship between the three-dimensional structure of Sm14 and the peptides selected for vaccination trials according to Example 1. Top center is shown a ribbon representation of the model for the Sm14 molecule. Residues conserved in Sm14 and Fh15 (but infrequent in human homologues) and also solvent exposed, are highlighted in stick representation. On the left (above) is indicated the contribution of these residues (from family 1) to the accessible surface of the left-hand side of the molecule, and below, how peptides 1.1 and 1.2 attempt to reproduce this surface. On the right, an analogous representation is given for family 2.

Example 2

Peptide Synthesis

The peptides according to the present invention were synthesized by usual procedures (from the state of the art) and provided in the form of C-terminal amides as free peptides, at a purity of greater than 97%.

Example 3

Expression of Recombinant Sm14 (r-Sm14)

In order to provide control experiments the recombinant Sm14 protein expressed by the pRSETA-6xHis-Sm14 construct was obtained after transformation of chemically competent E. coli BL21 (DE3) as described in Ramos C. R. R et al., Mem Inst. Oswaldo Cruz, Rio de Janeiro, Vol. 96, Suppl.: 131-135, 2001, herein incorporated by reference.
Materials and Methods The pRSET A, B, C expression system was purchased from Invitrogen. The pET3-His (Chem & Tsonwin 1994) was obtained from the National Institute of Genetic, Japan. All the reagents used here were of analytical grade.
Expression and Purification of Recombinant Sm14

The recombinant Sm14 derived from pGEMEX expression system (Promega) was purified as described ("A Schistosoma mansoni fatty acid binding protein, Sm14, is the potential basis of a dual-purpose anti-helminth vaccine". Proc. Natl. Acad. Sci. 93: 269-273 and U.S. Pat. No. 5,730,984).

The recombinant Sm14 proteins expressed by pRSETA-Sm14, pET3-His-Sm14 and pRSETA-6Xhis-Sm14 constructs were obtained after transformation of chemically competent E. coli BL21 (DE3). The transformed clones were grown in liquid LB (Luria Bertani medium) at 37° C. with agitation (200 rpm) until a 0.6 optical density was reached at 600 nm. At this point, IPTG was added to a final concentration of 0.5 mM. The cultures were grown for an additional 3 h in the same conditions described and the cells were harvested by centrifugation at 2,000 g. The Sm14 was expressed in inclusion bodies in all cases. The cells resuspended in 50 mM Tris-HCl ph 8.0, 100 mM NaCl, 10 mM EDTA, 10 MM2-mercaptoethanol were disrupted by french pressure and the insoluble Sm14 was recovered by centrifugation. The inclusion bodies were washed by centrifugation with the previous solution also containing 2 M urea and finally dissolved in 8 M urea at room temperature for 2 h in the same buffer. The clarified supernatants were diluted 200 times by dropping in refolding solution (50 mM Tris-HCl pH8.0, 500 ml NACl, 5 mM imidazol) by stirring at room temperature for 18-24 h. The total volume was clarified by centrifugation and loaded onto a C10 column (Amersham Pharmacia) containing 5 ml of $Ni^{+2}$-charged resin (Amersham Pharmacia) previously equilibrated with the refolding buffer at 1 ml/min. The column was washed with 10-20 volumes of refolding buffer containing 20 mM imidazol and the adsorbed protein was eluted by 1M imidazol in the refolding buffer. Fractions of 1 ml were collected. Characterization of the fractions was done by SDS-PAGE and Western-Blot according to described protocols (Harlow & Lane 1988, Ausubel et al. 1989, Sambrook et al. 1989).

Example 4

Immunization Experiments Against S. mansoni

In this experiment, outbreed Swiss mice were immunized with two intradermal/subcutaneous doses at an interval of 7 days followed by a booster injection, 21 days later. In the case of the peptides, a dose of 70 μg in the presence of the adjuvant monophosphoryl lipid A+trehalose dimycolate (MPL-TDM, Ribi ImmunoChem Research Inc.) and $Al(OH)_3$ was used for all injections. The peptides used in accordance with the present invention were those prepared as discussed in Example 1 with the exception of peptide 1.1.

For control experiments with r-Sm14 (prepared according to Example 3) and Saline Extract (SE) (as described in U.S. Pat. No. 4,396,600) the doses used were 10 μg and 300 μg respectively. In the case of SE, two routes of administration were employed, via the inguinal region and the footpad. For all other antigens, only the inguinal route was used.

For assays of protection against S. mansoni, the animals were challenged subcutaneously with 100 cercariae, 60 days after the last immunization and perfused 45 days later. Overall protection was calculated by the formula $\{(C-V)/C\} \times 100$, where C is the average number of worms in control animals and V is the average number of worms in vaccinated animals.

The results of this first vaccination experiment against S. mansoni in Swiss mice (FIG. 11) established an apparently significant increase in protection after administering saline extract (one of the standard controls used), via the footpad as compared with the inguinal route. During this initial experiment the peptides were also administered inguinally.

As a consequence a second protocol was established for the most promising peptides but employing the footpad as the administrative route of choice.

Figure 11:
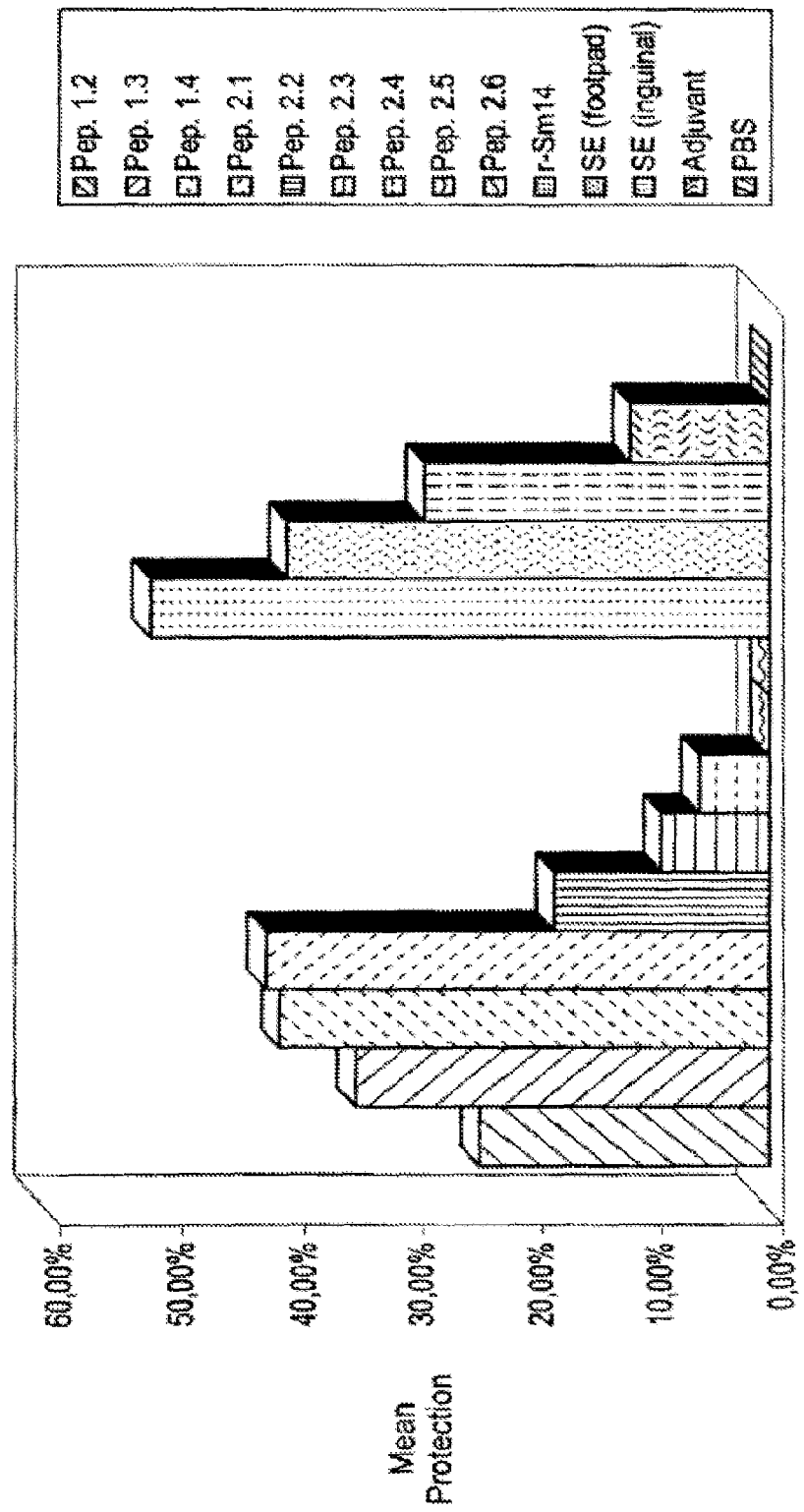
FIG. 11 shows A first vaccination experiment against S. mansoni. Percentage protection, $\{(C-V)/C\} \times 100\}$, of outbred Swiss mice is given after vaccination and subsequent challenge with 100 cercariae. From left to right the bars correspond to vaccination with peptide 1.2, peptide 1.3, peptide 1.4, peptide 2.1, peptide 2.2, peptide 2.3, peptide 2.4, peptide 2.5, peptide 2.6, r-Sm14, saline extract (SE) administered via the footpad, SE administered via the inguinal route, adjuvant and PBS respectively. All peptides were administered via the inguinal route. All peptides were administered in the presence of the adjuvant monophosphoryl lipid A+trehalose dicorynomycolate (MPL-TDM, Ribi ImmunoChem Research Inc.)+Alum.

FIG. 11 clearly shows a large degree of discrimination and selectivity amongst the nine peptides used in the first experiment, the levels of protection varying greatly from a maximum of slightly over 40% (peptides 1.4 and 2.1) down to no protection at all (2.5 and 2.6). This implies a specific immune response to the different amino acid sequences and not a generic reaction to immunization by any foreign peptide. This is emphasized by the fact that peptide 2.6, which is unrelated to Sm14 (as it was generated by sequence randomization of 2.5) did not lead to protection.

Figure 12:
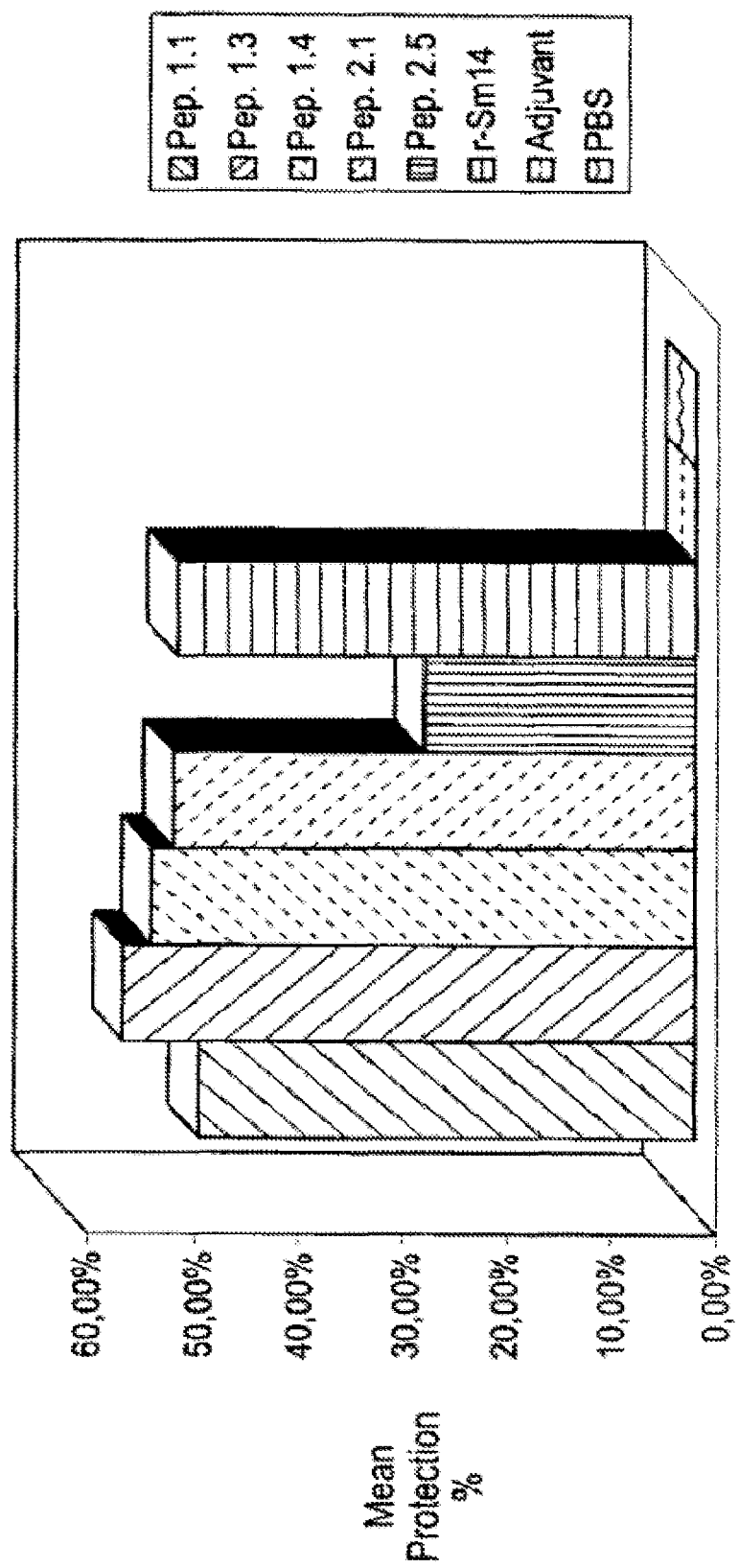
FIG. 12 shows a second vaccination experiment against S. mansoni. Percentage protection is given as in FIG. 9. From left to right the bars correspond to peptide 1.1, peptide 1.3, peptide 1.4, peptide 2.1, peptide 2.5, r-Sm14, adjuvant and PBS respectively. In this experiment all samples were administered via the footpad. All peptides were administered in the presence of adjuvant: monophosphoryl lipid A+trehalose dicorynomycolate (MPL-TDM, Ribi ImmunoChem Research Inc.)+Alum.

FIG. 11 also shows that the peptides from the first family, which offered the greatest levels of protection, were 1.3 and 1.4, both of which correspond to different variations of fusions of the smaller peptides 1.1 and 1.2. In a second experiment (see following example), peptide 1.1, which had been excluded from the initial trial, was subsequently shown to be as effective as the fusion peptides, 1.3 and 1.4 (see FIG. 12). Of the second family, the smallest peptide 2.1, of total length 10 residues offered the greatest levels of protection (42.1%). The remaining members of the second family produced progressively lower levels of protection (FIG. 11) falling to zero for peptides 2.5 and 2.6.

Example 5

Further Immunization Experiments Against *S. mansoni*

In this experiment an identical protocol as Example 4 was employed for a sub-group of peptides including those which appeared most promising (1.1; 1.3; 1.4 and 2.1) together with 2.5 as a control, but employing the footpad as the route of administration.

Animals were challenged subcutaneously with 100 cercariae, 60 days after the last immunization and perfused days later. Overall protection was calculated by the formula $\{(C-V)/C\} \times 100$, where C is the average number of worms in control animals and V is the average number of worms in vaccinated animals.

In this second experiment (FIG. 12), in which only a limited number of peptides were tested, the performance of the most protective peptides (1.1, 1.3, 1.4 and 2.1) was equivalent to that seen for the recombinant whole protein (r-Sm14) and comparable to that reported previously (Tendler, M. et al. (1996). "A *Schistosoma mansoni* fatty acid binding protein, Sm14, is the potential basis of a dual-purpose anti-helminth vaccine". Proc. Natl. Acad. Sci. 93: 269-273.) showing that it may be possible to reproduce the protective immune response generated against Sm14, with much smaller molecules derived from it and which correspond to as little as less than 10% of its total molecular weight. Peptide 1.1, consisting of eight residues is the smallest of all the peptides tested and yet gave rise to protective levels of close to 50%. In these trials against *S. mansoni* relatively little appears to be gained by increasing the size of this peptide, since 1.3 and 1.4 produced very similar results in terms of protection.

This implies that most of the immunogenic capacity of these larger fusion peptides is due to their N-terminal sequences, which is identical to 1.1 and which corresponds to residues 118 to 125 of the original Sm14. Peptide 1.1 is thus derived from the C-terminal region of the molecule and its important immunogenic role is consistent with the observation made above concerning residue conservation in this region of the molecule.

That the C-terminal third of the molecule contributes to the most important epitopes on Sm14 is further supported by the fact that peptide 2.1 (corresponding to residues 85 to 94) also affords high levels of protection (42.1% in the first experiment and 50% in the second). However, in this case there is a marked difference when compared with the first family. On generating the larger fusion peptides, by adding the 2.2 sequence to 2.1 in various different formats, the resulting peptides are less protective. One potential explanation for this may be that humoral responses to the peptides, which should be conformation specific, may be ineffective if the peptides assume structures which disguise, occlude or alter the structure of the epitope.

At present little is known about the nature of the immune response induced by Sm14 although it is believed to include both humoral and cellular contributions. The cellular component of this response has been correlated with resistance, susceptibility and delayed type hypersensitivity (DTH)-mediated pathology. It is also known that IL-10 is a key molecule in the regulation of T cell response in schistosomiasis. A population study performed by Brito et al. (Brito C F, Caldas I R, Coura Filho P, Correa-Oliveira R, Oliveira S C., "CD4+ T cells of schistosomiasis naturally resistant individuals living in an endemic area produce interferon-gamma and tumour necrosis factor-alpha in response to the recombinant 14 KDA *Schistosoma mansoni* fatty acid-binding protein.", Scand J. Immunol. 2000 June; 51(6):595-601. PMID: 10849370 [PubMed—indexed for MEDLINE]) in a Brazilian schistosomiasis endemic area showed that the highest levels of proliferative response to Sm14 was observed mainly in peripheral blood mononuclear cells (PBMC) from uninfected endemic normal individuals. This suggests that T cell activity against the Sm14 antigen should be the same mechanism associated with natural resistance against infection.

On the other hand humoral responses in schistosomiasis have been associated with various effector or regulatory mechanisms. IgG and IgE are directly involved in the in vitro killing of schistosome larvae in association with macrophages and platelets. According to Brito et al (Brito C F, Fonseca C T, Goes A M, Azevedo V, Simpson A J, Oliveira S C. "Human IgG1 and IgG3 recognition of *Schistosoma mansoni* 14 kDa fatty acid-binding recombinant protein.", Parasite Immunol. 2000 January; 22(1):41-8.) the prevalent types of antibody against Sm14 in sera of different clinical forms of schistosomiasis are IgG1 and IgG3. They also suggest that effector function induced by these immunoglobulin molecules might be a critical component of the immune system involved in protection induced by Sm14.

Example 6

Immunization Experiments Against *F. hepatica*

This example refers to the use of some of the peptides described in Example 1 for vaccination against *Fasciola hepatica* in the Swiss mouse model. For the *Fasciola hepatica* protection assay each group (10 outbred Swiss mice/group) received three intradermal/subcutaneous doses via the footpad using an identical protocol to that described above for *S. mansoni*. Animals were vaccinated with either 70 μg of one of the sub-group of peptides described above (1.1, 1.3, 1.4, 2.1 and 2.5), emulsified in Ribi adjuvant (MPL-TDM) and Al(OH)$_3$ or 10 Ξg of r-Sm14 (in the presence or absence of adjuvant), or an equivalent amount of adjuvant alone. Vaccinated and non-vaccinated control groups were simultaneously challenged orally with 3 metacercariae of *F. hepatica* 60 days after immunization and the sacrifice of all animals performed 30 days after challenge.

Figure 13:
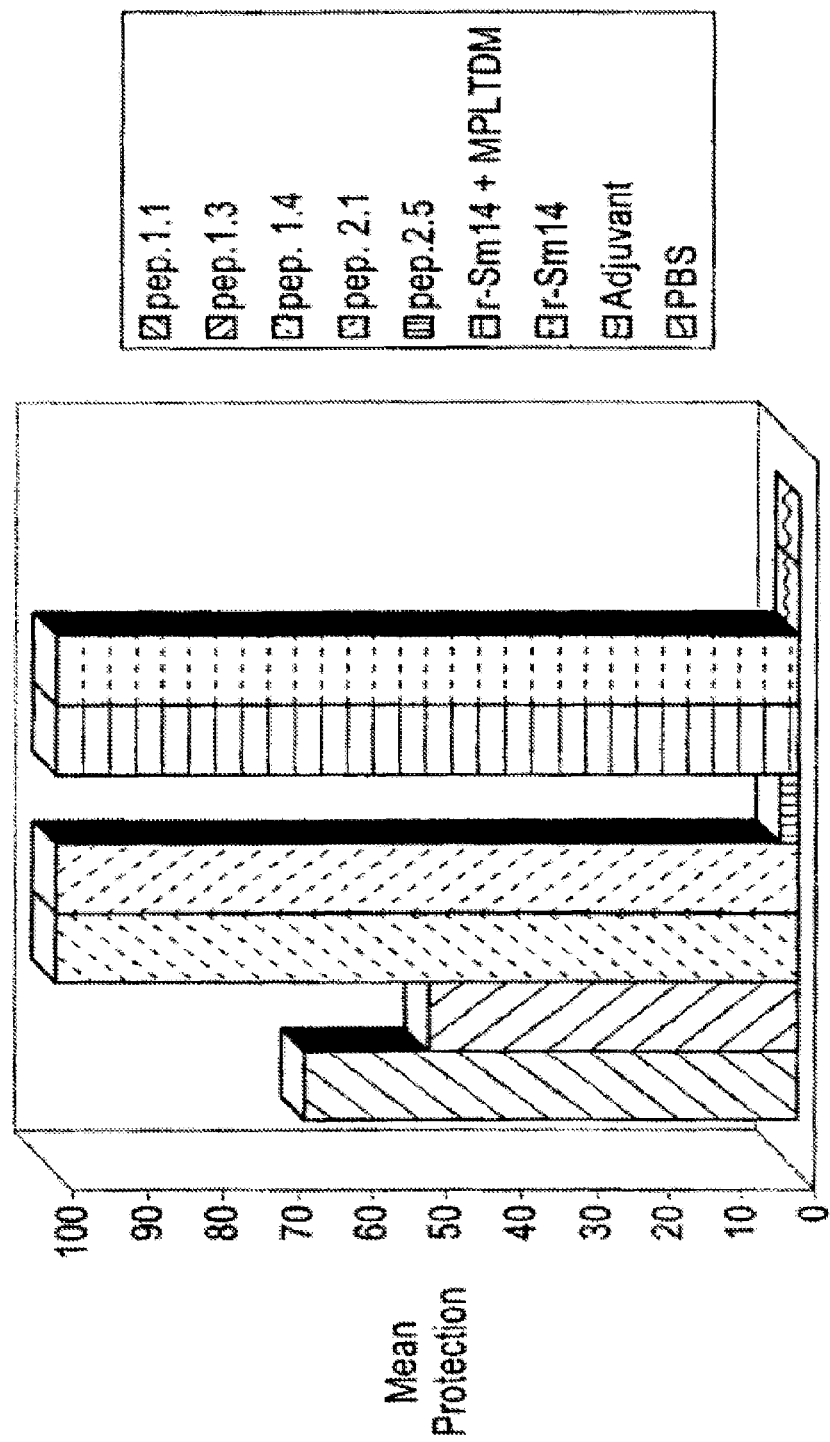
FIG. 13 shows the percentage protection of 10 outbred Swiss mice after vaccination and subsequent challenge with three *F. hepatica* metacercariae. Due to the limited number of parasites used for challenge, animals are considered protected when they present sterile immunity, ie no adult worms are present after sacrifice. The mean protection is therefore given as the percentage of sterile animals at sacrifice. From left to right the bars correspond to peptide 1.1, peptide 1.3, peptide 1.4, peptide 2.1, peptide 2.5, r-Sm14+adjuvant, r-Sm14, adjuvant and PBS respectively. The adjuvant used was monophosphoryl lipid A+trehalose dicorynomycolate (MPL-TDM, Ribi ImmunoChem Research Inc.)+Alum.

FIG. 13 shows the results of vaccination trials in Swiss mice after challenge with three *F. hepatica* metacercriae.

As anticipated from previously published data (Tendler, M. et al. (1996). "A *Schistosoma mansoni* fatty acid binding protein, Sm14, is the potential basis of a dual-purpose anti-helminth vaccine". Proc. Natl. Acad. Sci. 93: 269-273), r-Sm14 in the presence or absence of adjuvant is able to offer 100% protection to outbred Swiss mice under the given vaccination protocol, which is limited by the number of metacercariae which can be used as challenge. By comparison animals which were vaccinated with adjuvant alone or control animals which received no vaccine, were either dead or infected with at least one adult worm at the end of the experiment (30 days after challenge infection). Of the limited set of peptides selected for vaccination trials in *F. hepatica*, peptides 1.4 and 2.1 were the most effective, generating 100% protection with the protocol adopted, similar to that achieved with the whole protein. In this case peptides 1.1 and 1.3 were less effective (66.7% and 50% respectively) and peptide 2.5 was the least effective of all (12.5% protection).

In general terms these results are consistent with those for *S. mansoni*. However, in the case of the first family, there does seem to be some gain in using the designed fusion peptide 1.4 over the simpler peptide 1.1. In this case, it would seem that there is also considerable gain in introducing the glycines between the two original peptide segments, suggesting that additional flexibility may indeed help the peptide to assume an immunologically relevant conformation. In the case of family 2, once again the larger peptide 2.5 was effectively inactive whilst the smaller 2.1 (which is almost identical at its N-terminus) generated 100% protection.

Example 7

The Presence of FABPs Related to Sm14 in Other Helminths of Medical and Veterinary Importance FIG. 14 shows the alignment of several FABPs from different parasites, highlighting elements of secondary structure and residues predicted to participate in the discontinuous epitopes of Sm14. These residues are therefore potentially cross-reactive towards all parasites listed in the alignment.

In order to demonstrate the presence of cross-reactive molecules related to Sm14 in other helminthes, extracts from said helminthes were tested in the following manner.

Figure 16A:
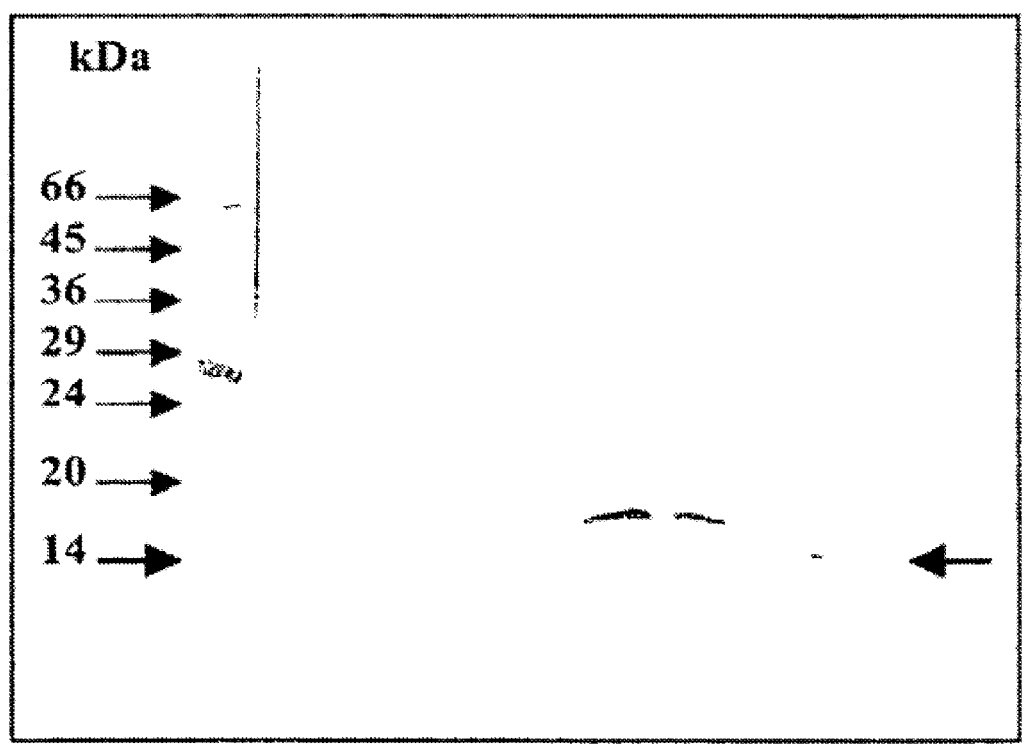
FIG. 16A shows Western Blotting data related to extracts from different helminths.
Figure 16B:
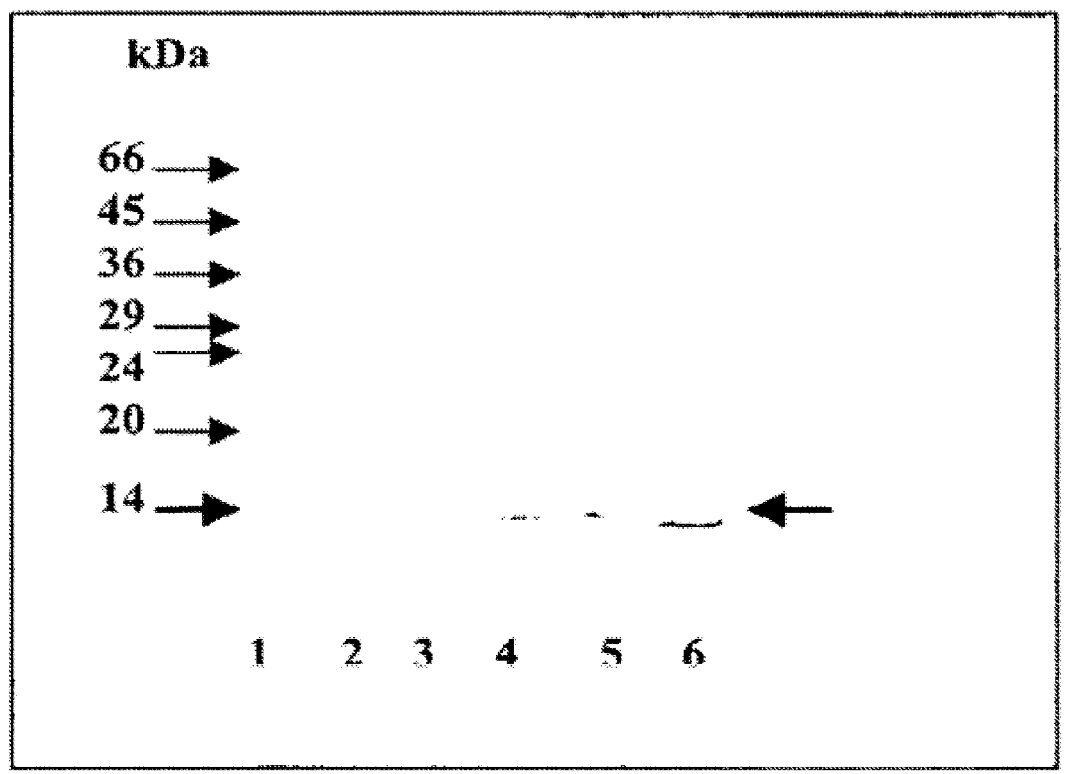
FIG. 16B also shows Western Blotting data related to extracts from different helminths.

Extracts from the following nine helmiths were tested: the trematode *Echinostoma paraensei*; the cestoids *Hymenolepis diminuta, Dipylidium caninum* e *Taenia saginata*; the nematodes *Aspiculuris tetraptera, Toxocara* sp., *Ascaris suum* (machos), *A. suum* (fêmeas) e *Toxocara canis*. Four of these extracts (*A. suum* machos e fêmeas, *E. paraensei* e *T. saginata*) contained a protein component that was recognised by monospecific polyclonal anti-rSm14 antibody, as demonstrated in FIG. 16A. In the case of the extracts derived from both male and female *A. suum*, the cross-reacting component possesses a molecular weight of a little over 14 kDa, as shown in FIG. 16B. The protein bands detected in this experiment are extremely similar to those seen in the controls (saline extract, SE, from male and female parasites), in other words, they presented no differences in terms of expressibility as has been seen in previous cases.

As previously stated FABPs have already been described in several different helminthes (including trematodes, cestoids and nematodes). Such molecules possess conserved amino acid sequences and three-dimensional structures from one species to another. As an example Sm14 and Fh15 (FABP de *Fasciola hepatica*) share 44% sequence identity, believed to be responsible for the heterologous resistance observed between the two species. A further example is the FABP from *Ascaris suum*, As-p18, which presents 28% sequence identity with Sm14 and a very similar predicted three-dimensional structure.

FIG. 16B also shows that a 14 kDa component from *E paraensei* is recognized by anti-rSm14 serum, the latter obtained from rabbits previously inoculated with the recombinant molecule.

The final extract to show immune cross-reactivity with anti-rSm14 serum was that from *Taenia saginata*. FIG. 16B also shows that in this case the protein band recognized has a molecular weight of approximately 14 kDa.

These results demonstrate that the Sm14 molecule presents immune cross-reactivity with other proteins of the same family (FABPs from *A. suum, E. paraensei* e *T. saginata*.) Furthermore, in the case of infection by *F. hepatica*, the efficiency of Sm14 as a vaccine against the fascioliasis has already been proven (see previous examples). This demonstrates the effectiveness of the use of Sm14 as a bivalent anti-helminth vaccine for use against schistosomiasis and fascioliasis.

The fact that a) the above data demonstrate the phenomenon of immune cross-reactivity between anti-rSm14 serum and FABPs derived from several other helminth parasites, b) FIG. 14 shows that many of the residues identified in Sm14 as belonging to the discontinuous epitopes are conserved in the sequences of FABPs from other parasitic helminthes, c) the fact that such molecules are well distributed amongst helminth parasites, d) the fact that the three-dimensional structure of such FABPs is extremely well conserved, indicate that we can apply the Sm14 molecule as the molecular basis for a multivalent anti-helminth vaccine.

The results of the Examples of the present invention show that uncoupled peptides confer protection against both parasites which are equivalent to those seen with the parent molecule."

The results presented in these examples also provide evidence that it is possible to considerably simplify the Sm14 molecule and still induce a protective immune response to both *S. mansoni* and *F. hepatica* in experimental animals. This represents the development of a bivalent anti-helminth peptide vaccine, which provides several advantages in terms of chemical stability, safety and reproducibility of manufacture, which have important consequences for efficient delivery in endemic regions.

In the case of humoral responses the three-dimensional conformations accessible to the peptide are relevant to their effectiveness and in principal, it is of interest to include as many of the regions of a discontinuous epitope as possible into a single peptide.

Figure 15:
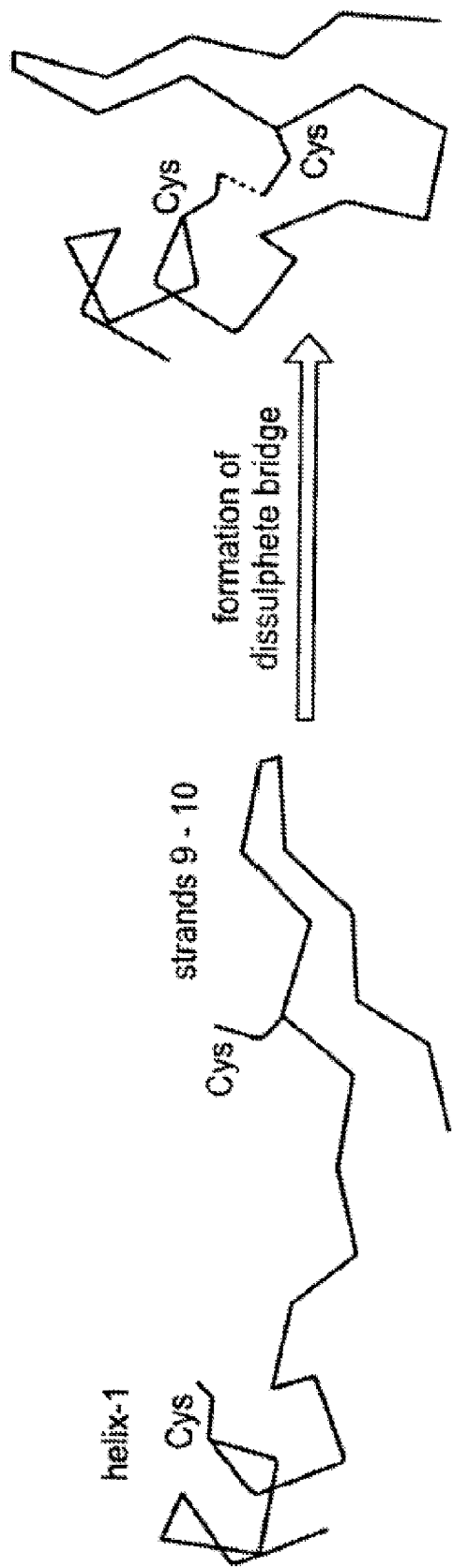
FIG. 15 schematically represents the position of Cysteine residues in peptides and their role in restraining conformational movement (dashes indicate Cα).

Referring to FIG. 15, it represents the position of cysteine residues in peptides and their role in restraining conformational movement. Residues which restrict the conformational mobility in relation to the elements of the secondary structure were studied. Specifically, FIG. 15 shows the result of the addition of cysteine as a tool for the restriction of the spatial mobility. It was found that the cysteines when present in pair in the sequence, for example in oxidant medium, form cistines (dissulphete bridge), joining peptide fragments which could be distant in the conformational structure in solution.

The result shows that the presence of FABPs in helminths is a rule, being the helminth a trematode, a cestoid or a nematode. In addition to this, there exists the confirmation of the importance of FABPs as a base for the vaccination, as they exhibit immunogenic epitopes and develop important functions in the physiology of the microrganisms.

It should be noted that modifications and variations together with others that would be obvious for a person of ordinary skill in the art are deemed to be within the scope of the present invention the nature of which is to be determined from the above description and claims.

We claim:

1. An immunogenic composition comprising a fusion peptide molecule and a pharmaceutical carrier, said immunogenic composition being able to confer at least partial protection against infection with a pathogenic helminth, wherein the fusion peptide molecule is obtained according to a method comprising:

(i) selecting a region of a parent protein that contains amino acid residues that are spatially close in the three-dimensional structure but distant in the amino acid sequence and which form discontinuous epitopes, wherein the parent protein is a Sm14 protein or a related Fatty Acid Binding Protein (FABP) from a helminth pathogen;

(ii) giving priority to maintaining epitopic amino acid residues predicted to be responsible for stimulating the desired immunogenic response, within the selected peptide sequence;

(iii) elaborating sequences which are of limited size varying from 8 to 28 amino acid residues and which maintain at least some of the previously predicted epitopic residues;

(iv) choosing at least two peptides from the elaborated sequences that correspond to regions that are distant in the primary structure (amino acid sequence) but spatially close in the tertiary (three-dimensional) structure of the parent protein, wherein said regions are chosen on the basis that the three-dimensional structure indicates that they can be readily fused assuming that they retain their original structures; and (v) constructing the fusion peptide molecule comprising the chosen at least two peptides in step (iv).

2. The immunogenic composition according to claim 1, wherein the pathogenic helminth is *Schistosoma mansoni*, *Fasciola hepatica* or both.

3. The immunogenic composition according to claim 1, wherein the immunogenic composition consists of the fusion peptide and the pharmaceutical carrier.

4. The immunogenic composition of claim 1, wherein half cysteine residues are inserted in the fusion peptide to restrict the conformational freedom of the final fusion peptide.

5. The immunogenic composition of claim 1, wherein the parent protein is a FABP.

6. The immunogenic composition of claim 1, wherein the parent protein is a Sm14 protein.

7. The immunogenic composition of claim 1, wherein the method for obtaining the fusion peptide further comprises modifying the fusion peptide obtained in the manner described in step (iv), so as to favor the three-dimensional conformation as seen in the parent protein, wherein said modification may include substitutions of amino acids as well as insertions or deletions of amino acids.

8. The immunogenic composition of claim 7, wherein amino acid residues are inserted into the fusion peptide in order to restrict the conformational freedom of the final fusion peptide.

* * * * *

SEQUENCE LISTING

```
<160> NUMBER OF SEQ ID NOS: 30

<210> SEQ ID NO 1
<211> LENGTH: 8
<212> TYPE: PRT
<213> ORGANISM: Artificial sequence
<220> FEATURE:
<223> OTHER INFORMATION: oligopeptide from Schistosoma mansoni

<400> SEQUENCE: 1

Val Thr Val Gly Asp Val Thr Ala
1               5

<210> SEQ ID NO 2
<211> LENGTH: 10
<212> TYPE: PRT
<213> ORGANISM: Artificial sequence
<220> FEATURE:
<223> OTHER INFORMATION: Oligopeptide from Schistosoma mansoni

<400> SEQUENCE: 2

Asn Phe Asp Ala Val Met Ser Lys Leu Gly
1               5                   10

<210> SEQ ID NO 3
<211> LENGTH: 18
<212> TYPE: PRT
<213> ORGANISM: Artificial sequence
<220> FEATURE:
<223> OTHER INFORMATION: Oligopeptide derived from the fusion of two
      peptides from Schistosoma mansoni

<400> SEQUENCE: 3

Val Thr Val Gly Asp Val Thr Ala Asn Phe Asp Ala Val Met Ser Lys
1               5                   10                  15

Leu Gly

<210> SEQ ID NO 4
<211> LENGTH: 18
<212> TYPE: PRT
<213> ORGANISM: Artificial sequence
<220> FEATURE:
<223> OTHER INFORMATION: Oligopeptide derived from the fusion of two
      peptides from Schistosoma mansoni

<400> SEQUENCE: 4

Val Thr Val Gly Asp Val Thr Gly Gly Ser Asp Ala Val Met Ser Lys
1               5                   10                  15

Leu Gly

<210> SEQ ID NO 5
<211> LENGTH: 10
<212> TYPE: PRT
<213> ORGANISM: Artificial sequence
<220> FEATURE:
<223> OTHER INFORMATION: Oligopeptide from Schistosoma mansoni

<400> SEQUENCE: 5
```

```
Glu Lys Asn Ser Glu Ser Lys Leu Thr Gln
1               5                   10

<210> SEQ ID NO 6
<211> LENGTH: 13
<212> TYPE: PRT
<213> ORGANISM: Artificial sequence
<220> FEATURE:
<223> OTHER INFORMATION: Oligopeptide from Schistosoma mansoni

<400> SEQUENCE: 6

Ile Val Arg Glu Val Asp Gly Asp Thr Met Lys Thr Thr
1               5                   10

<210> SEQ ID NO 7
<211> LENGTH: 23
<212> TYPE: PRT
<213> ORGANISM: Artificial sequence
<220> FEATURE:
<223> OTHER INFORMATION: Oligopeptide derived from the fusion of two
      peptides from Schistosoma mansoni

<400> SEQUENCE: 7

Glu Lys Asn Ser Glu Ser Lys Leu Thr Gln Ile Val Arg Glu Val Asp
1               5                   10                  15

Gly Asp Thr Met Lys Thr Thr
            20

<210> SEQ ID NO 8
<211> LENGTH: 27
<212> TYPE: PRT
<213> ORGANISM: Artificial sequence
<220> FEATURE:
<223> OTHER INFORMATION: Oligopeptide derived from the fusion of two
      peptides from Schistosoma mansoni

<400> SEQUENCE: 8

Glu Lys Phe Ser Glu Ser Lys Leu Thr Ser Asp Pro Thr Gly Ile Val
1               5                   10                  15

Arg Glu Val Asp Gly Ala Thr Met Lys Thr Thr
            20                  25

<210> SEQ ID NO 9
<211> LENGTH: 25
<212> TYPE: PRT
<213> ORGANISM: Artificial sequence
<220> FEATURE:
<223> OTHER INFORMATION: Oligopeptide derived from the fusion of two
      peptides from Schistosoma mansoni

<400> SEQUENCE: 9

Glu Lys Phe Ser Glu Ser Lys Leu Thr Phe Asp Gly Ile Val Arg Glu
1               5                   10                  15

Val Asp Gly Ala Thr Met Lys Thr Thr
            20                  25

<210> SEQ ID NO 10
<211> LENGTH: 25
<212> TYPE: PRT
<213> ORGANISM: Artificial sequence
<220> FEATURE:
<223> OTHER INFORMATION: Synthesized oligopeptide

<400> SEQUENCE: 10

Lys Ile Gly Thr Ser Val Phe Gly Thr Arg Thr Ser Lys Phe Asp Ala
```

<210> SEQ ID NO 11
<211> LENGTH: 131
<212> TYPE: PRT
<213> ORGANISM: Homo sapiens

<400> SEQUENCE: 11

Ser Asn Lys Phe Leu Gly Thr Trp Lys Leu Val Ser Ser Glu Asn Phe
1               5                   10                  15

Asp Asp Tyr Met Lys Ala Leu Gly Val Gly Leu Ala Thr Arg Lys Leu
            20                  25                  30

Gly Asn Leu Ala Lys Pro Thr Val Ile Ile Ser Lys Lys Gly Asp Ile
        35                  40                  45

Ile Thr Ile Arg Thr Glu Ser Thr Phe Lys Asn Thr Glu Ile Ser Phe
    50                  55                  60

Lys Leu Gly Gln Glu Phe Glu Glu Thr Thr Ala Asp Asn Arg Lys Thr
65                  70                  75                  80

Lys Ser Ile Val Thr Leu Gln Arg Gly Ser Leu Asn Gln Val Gln Arg
                85                  90                  95

Trp Asn Gly Lys Glu Thr Thr Ile Lys Arg Lys Leu Val Asp Gly Lys
            100                 105                 110

Met Val Ala Glu Cys Lys Met Lys Gly Val Val Cys Thr Arg Ile Tyr
        115                 120                 125

Glu Lys Val
    130

<210> SEQ ID NO 12
<211> LENGTH: 131
<212> TYPE: PRT
<213> ORGANISM: Homo sapiens

<400> SEQUENCE: 12

Cys Asp Ala Phe Val Gly Thr Trp Lys Leu Val Ser Ser Glu Asn Phe
1               5                   10                  15

Asp Asp Tyr Met Lys Glu Val Gly Val Gly Phe Ala Thr Arg Lys Val
            20                  25                  30

Ala Gly Met Ala Lys Pro Asn Met Ile Ile Ser Val Asn Gly Asp Val
        35                  40                  45

Ile Thr Ile Lys Ser Glu Ser Thr Phe Lys Asn Thr Glu Ile Ser Phe
    50                  55                  60

Ile Leu Gly Gln Glu Phe Asp Glu Val Thr Ala Asp Asp Arg Lys Val
65                  70                  75                  80

Lys Ser Thr Ile Thr Leu Asp Gly Gly Val Leu Val His Val Gln Lys
                85                  90                  95

Trp Asp Gly Lys Ser Thr Thr Ile Lys Arg Lys Arg Glu Asp Asp Lys
            100                 105                 110

Leu Val Val Glu Cys Val Met Lys Gly Val Thr Ser Thr Arg Val Tyr
        115                 120                 125

Glu Arg Ala
    130

<210> SEQ ID NO 13
<211> LENGTH: 134
<212> TYPE: PRT

<213> ORGANISM: Homo sapiens

<400> SEQUENCE: 13

Pro Val Asp Phe Thr Gly Tyr Trp Lys Met Leu Val Asn Glu Asn Phe
1               5                   10                  15

Glu Glu Tyr Leu Arg Ala Leu Asp Val Asn Val Ala Leu Arg Lys Ile
            20                  25                  30

Ala Asn Leu Leu Lys Pro Asp Lys Glu Ile Val Gln Asp Gly Asp His
        35                  40                  45

Met Ile Ile Arg Thr Leu Ser Thr Phe Arg Asn Tyr Ile Met Asp Phe
    50                  55                  60

Gln Val Gly Lys Glu Phe Glu Glu Asp Leu Thr Gly Ile Asp Asp Arg
65                  70                  75                  80

Lys Cys Met Thr Thr Val Ser Trp Asp Gly Asp Lys Leu Gln Cys Val
                85                  90                  95

Gln Lys Gly Glu Lys Glu Gly Arg Gly Trp Thr Gln Trp Ile Glu Gly
            100                 105                 110

Asp Glu Leu His Leu Glu Met Arg Val Glu Gly Val Val Cys Lys Gln
        115                 120                 125

Val Phe Lys Lys Val Gln
    130

<210> SEQ ID NO 14
<211> LENGTH: 136
<212> TYPE: PRT
<213> ORGANISM: Homo sapiens

<400> SEQUENCE: 14

Pro Asn Phe Ala Gly Thr Trp Lys Met Arg Ser Ser Glu Asn Phe Asp
1               5                   10                  15

Glu Leu Leu Lys Ala Leu Gly Val Asn Ala Met Leu Arg Lys Val Ala
            20                  25                  30

Val Ala Ala Ala Ser Lys Pro His Val Glu Ile Arg Gln Asp Gly Asp
        35                  40                  45

Gln Phe Tyr Ile Lys Thr Ser Thr Thr Val Arg Thr Thr Glu Ile Asn
    50                  55                  60

Phe Lys Val Gly Glu Gly Phe Glu Glu Thr Val Asp Gly Arg Lys
65                  70                  75                  80

Cys Arg Ser Leu Ala Thr Trp Glu Asn Glu Asn Lys Ile His Cys Thr
                85                  90                  95

Gln Thr Leu Leu Glu Gly Asp Gly Pro Lys Thr Tyr Trp Thr Arg Glu
            100                 105                 110

Leu Ala Asn Asp Glu Leu Ile Leu Thr Phe Gly Ala Asp Asp Val Val
        115                 120                 125

Cys Thr Arg Ile Tyr Val Arg Glu
    130                 135

<210> SEQ ID NO 15
<211> LENGTH: 137
<212> TYPE: PRT
<213> ORGANISM: Homo sapiens

<400> SEQUENCE: 15

Pro Asn Phe Ser Gly Asn Trp Lys Ile Ile Arg Ser Glu Asn Phe Glu
1               5                   10                  15

Glu Leu Leu Lys Val Leu Gly Val Asn Val Met Leu Arg Lys Ile Ala
            20                  25                  30

Val Ala Ala Ala Ser Lys Pro Ala Glu Ile Lys Gln Glu Gly Asp
             35                   40                  45

Thr Phe Tyr Ile Lys Thr Ser Thr Thr Val Arg Thr Thr Glu Ile Asn
    50                  55                  60

Phe Lys Val Gly Glu Glu Phe Glu Glu Gln Thr Val Asp Gly Arg Pro
65                  70                  75                  80

Cys Lys Ser Leu Val Lys Trp Glu Ser Glu Asn Lys Met Val Cys Glu
                85                  90                  95

Gln Lys Leu Leu Lys Gly Glu Gly Pro Lys Thr Ser Trp Thr Arg Glu
                100                 105                 110

Leu Thr Asn Asp Gly Glu Leu Ile Leu Thr Met Thr Ala Asp Asp Val
                115                 120                 125

Val Cys Thr Arg Val Tyr Val Arg Glu
                130                 135

<210> SEQ ID NO 16
<211> LENGTH: 135
<212> TYPE: PRT
<213> ORGANISM: Homo sapiens

<400> SEQUENCE: 16

Met Ala Thr Val Gln Gln Leu Glu Gly Arg Trp Arg Leu Val Asp Ser
1               5                   10                  15

Lys Gly Phe Asp Glu Tyr Met Lys Glu Leu Gly Val Gly Ile Ala Leu
                20                  25                  30

Arg Lys Met Gly Ala Met Ala Lys Pro Asp Cys Ile Ile Thr Cys Asp
            35                  40                  45

Gly Lys Asn Leu Thr Ile Lys Thr Glu Ser Thr Leu Lys Thr Thr Gln
        50                  55                  60

Phe Ser Cys Thr Leu Gly Glu Lys Phe Glu Glu Thr Thr Ala Asp Gly
65                  70                  75                  80

Arg Lys Thr Gln Thr Val Cys Asn Phe Thr Asp Gly Ala Leu Val Gln
                85                  90                  95

His Gln Glu Trp Asp Gly Lys Glu Ser Thr Ile Thr Arg Lys Leu Lys
                100                 105                 110

Asp Gly Lys Leu Val Val Glu Cys Val Met Asn Asn Val Thr Cys Thr
            115                 120                 125

Arg Ile Tyr Glu Lys Val Glu
        130                 135

<210> SEQ ID NO 17
<211> LENGTH: 131
<212> TYPE: PRT
<213> ORGANISM: Homo sapiens

<400> SEQUENCE: 17

Ala Phe Asp Ser Thr Trp Lys Val Asp Arg Ser Glu Asn Tyr Asp Lys
1               5                   10                  15

Phe Met Glu Lys Met Gly Val Asn Ile Val Lys Arg Lys Leu Ala Ala
                20                  25                  30

His Asp Asn Leu Lys Leu Thr Ile Thr Gln Glu Gly Asn Lys Phe Thr
            35                  40                  45

Val Lys Glu Ser Ser Ala Phe Arg Asn Ile Glu Val Val Phe Glu Leu
        50                  55                  60

Gly Val Thr Phe Asn Tyr Asn Leu Ala Asp Gly Thr Glu Leu Arg Gly
65                  70                  75                  80

```
Thr Trp Ser Leu Glu Gly Asn Lys Leu Ile Gly Lys Phe Lys Arg Thr
                85                  90                  95

Asp Asn Gly Asn Glu Leu Asn Thr Val Arg Glu Ile Ile Gly Asp Glu
            100                 105                 110

Leu Val Gln Thr Tyr Val Tyr Glu Gly Val Ala Lys Arg Ile Phe
        115                 120                 125

Lys Lys Asp
        130

<210> SEQ ID NO 18
<211> LENGTH: 127
<212> TYPE: PRT
<213> ORGANISM: Homo sapiens

<400> SEQUENCE: 18

Met Ser Phe Ser Gly Lys Tyr Gln Leu Gln Ser Gln Glu Asn Phe Glu
1               5                   10                  15

Ala Phe Met Lys Ala Ile Gly Leu Pro Glu Glu Leu Ile Gln Lys Gly
            20                  25                  30

Lys Asp Ile Lys Gly Val Ser Glu Ile Val Gln Asn Gly Lys His Phe
        35                  40                  45

Lys Phe Thr Ile Thr Ala Gly Ser Lys Val Ile Gln Asn Glu Phe Thr
    50                  55                  60

Val Gly Glu Glu Cys Glu Leu Glu Thr Met Thr Gly Glu Lys Val Lys
65                  70                  75                  80

Thr Val Val Gln Leu Glu Gly Asp Asn Lys Leu Val Thr Thr Phe Lys
                85                  90                  95

Asn Ile Lys Ser Val Thr Glu Leu Asn Gly Asp Ile Ile Thr Asn Thr
            100                 105                 110

Met Thr Leu Gly Asp Ile Val Phe Lys Arg Ile Ser Lys Arg Ile
        115                 120                 125

<210> SEQ ID NO 19
<211> LENGTH: 132
<212> TYPE: PRT
<213> ORGANISM: Homo sapiens

<400> SEQUENCE: 19

Val Asp Ala Phe Leu Gly Thr Trp Lys Leu Val Asp Ser Lys Asn Phe
1               5                   10                  15

Asp Asp Tyr Met Lys Ser Leu Gly Val Gly Phe Ala Thr Arg Gln Val
            20                  25                  30

Ala Ser Met Thr Lys Pro Thr Thr Ile Ile Glu Lys Asn Gly Asp Ile
        35                  40                  45

Leu Thr Leu Lys Thr His Ser Thr Phe Lys Asn Thr Glu Ile Ser Phe
    50                  55                  60

Lys Leu Gly Val Glu Phe Asp Glu Thr Ala Asp Asp Arg Lys Val
65                  70                  75                  80

Lys Ser Ile Val Thr Leu Asp Gly Gly Lys Leu Val His Leu Gln Lys
                85                  90                  95

Trp Asp Gly Gln Glu Thr Thr Leu Val Arg Glu Leu Ile Asp Gly Lys
            100                 105                 110

Leu Ile Leu Thr Leu Thr His Gly Thr Ala Val Ser Thr Arg Thr Tyr
        115                 120                 125

Glu Lys Glu Ala
        130
```

<210> SEQ ID NO 20
<211> LENGTH: 131
<212> TYPE: PRT
<213> ORGANISM: Mus musculus

<400> SEQUENCE: 20

Cys Asp Ala Phe Val Gly Thr Trp Lys Leu Val Ser Ser Glu Asn Phe
1               5                   10                  15

Asp Asp Tyr Met Lys Glu Val Gly Val Gly Phe Ala Thr Arg Lys Val
            20                  25                  30

Ala Gly Met Ala Lys Pro Asn Met Ile Ile Ser Val Asn Gly Asp Leu
        35                  40                  45

Val Thr Ile Arg Ser Glu Ser Thr Phe Lys Asn Thr Glu Ile Ser Phe
50                  55                  60

Lys Leu Gly Val Glu Phe Asp Glu Ile Thr Ala Asp Asp Arg Lys Val
65                  70                  75                  80

Lys Ser Ile Ile Thr Leu Asp Gly Gly Ala Leu Val Gln Val Gln Lys
                85                  90                  95

Trp Asp Gly Lys Ser Thr Thr Ile Lys Arg Lys Arg Asp Gly Asp Lys
            100                 105                 110

Leu Val Val Glu Cys Val Met Lys Gly Val Thr Ser Thr Arg Val Tyr
        115                 120                 125

Glu Arg Ala
    130

<210> SEQ ID NO 21
<211> LENGTH: 132
<212> TYPE: PRT
<213> ORGANISM: Rattus norvegicus

<400> SEQUENCE: 21

Met Ala Phe Asp Gly Thr Trp Lys Val Asp Arg Asn Glu Asn Tyr Glu
1               5                   10                  15

Lys Phe Met Glu Lys Met Gly Ile Asn Val Val Lys Arg Lys Leu Gly
            20                  25                  30

Ala His Asp Asn Leu Lys Leu Thr Ile Thr Gln Glu Gly Asn Lys Phe
        35                  40                  45

Thr Val Lys Glu Ser Ser Asn Phe Arg Asn Ile Asp Val Val Phe Glu
    50                  55                  60

Leu Gly Val Asp Phe Ala Tyr Ser Leu Ala Asp Gly Thr Glu Leu Thr
65                  70                  75                  80

Gly Thr Trp Thr Met Glu Gly Asn Lys Leu Val Gly Lys Phe Lys Arg
                85                  90                  95

Val Asp Asn Gly Lys Glu Leu Ile Ala Val Arg Glu Ile Ser Gly Asn
            100                 105                 110

Glu Leu Ile Gln Thr Tyr Thr Tyr Glu Gly Val Glu Ala Lys Arg Ile
        115                 120                 125

Phe Lys Lys Glu
    130

<210> SEQ ID NO 22
<211> LENGTH: 133
<212> TYPE: PRT
<213> ORGANISM: Schistosoma mansoni

<400> SEQUENCE: 22

Met Ser Ser Phe Leu Gly Lys Trp Lys Leu Ser Glu Ser His Asn Phe
1               5                   10                  15

Asp Ala Val Met Ser Lys Leu Gly Val Ser Val Ala Thr Arg Gln Ile
                20                  25                  30

Gly Asn Thr Val Thr Pro Thr Val Thr Phe Thr Met Asp Gly Asp Lys
            35                  40                  45

Met Thr Met Leu Thr Glu Ser Thr Phe Lys Asn Leu Ser Cys Thr Phe
    50                  55                  60

Lys Phe Gly Glu Glu Phe Asp Glu Lys Thr Ser Asp Gly Arg Asn Val
65                  70                  75                  80

Lys Ser Val Val Glu Lys Asn Ser Glu Ser Lys Leu Thr Gln Thr Gln
                85                  90                  95

Val Asp Pro Lys Asn Thr Thr Val Ile Val Arg Glu Val Asp Gly Asp
                100                 105                 110

Thr Met Lys Thr Thr Val Thr Val Gly Asp Val Thr Ala Ile Arg Asn
            115                 120                 125

Tyr Lys Arg Leu Ser
            130

<210> SEQ ID NO 23
<211> LENGTH: 133
<212> TYPE: PRT
<213> ORGANISM: Fasciola hepatica

<400> SEQUENCE: 23

Thr Met Ala Asp Phe Val Gly Ser Trp Lys Tyr Gly His Ser Glu Asn
1               5                   10                  15

Met Glu Ala Tyr Leu Lys Lys Ile Gly Val Ser Ser Asp Met Val Asp
                20                  25                  30

Lys Ile Leu Asn Ala Lys Pro Glu Phe Thr Phe Thr Leu Glu Gly Asn
            35                  40                  45

Lys Met Thr Ile Lys Met Val Ser Ser Leu Lys Thr Lys Ile Thr Thr
    50                  55                  60

Phe Thr Phe Gly Glu Glu Phe Glu Glu Thr Pro Asp Gly Lys Lys
65                  70                  75                  80

Val Met Thr Lys Val Thr Lys Asp Ser Glu Ser Lys Met Thr Gln Val
                85                  90                  95

Ile Lys Gly Pro Glu Cys Ile Thr Glu Val Val Arg Glu Val Val Gly
                100                 105                 110

Asp Lys Met Ile Ala Thr Trp Thr Val Gly Asp Val Lys Ala Val Thr
            115                 120                 125

Thr Leu Leu Lys Ala
            130

<210> SEQ ID NO 24
<211> LENGTH: 132
<212> TYPE: PRT
<213> ORGANISM: Schistosoma japonicum

<400> SEQUENCE: 24

Met Ser Ser Phe Leu Gly Lys Trp Lys Leu Ser Glu Ser His Asn Phe
1               5                   10                  15

Asp Ala Val Met Ser Lys Leu Gly Val Ser Trp Ala Thr Arg Gln Ile
                20                  25                  30

Gly Asn Thr Val Thr Pro Thr Val Thr Phe Thr Met Asp Gly Asp Thr
            35                  40                  45

-continued

```
Met Thr Met Leu Thr Glu Ser Thr Phe Lys Asn Leu Ser Val Thr Phe
    50                  55                  60
Lys Phe Gly Glu Glu Phe Asp Glu Lys Thr Ser Asp Gly Arg Ser Val
65                  70                  75                  80
Lys Ser Val Val Thr Lys Asp Ser Glu Ser Lys Ile Thr His Thr Gln
                85                  90                  95
Lys Asp Ser Lys Asn Thr Thr Val Ile Val Arg Glu Ile Val Gly Asp
            100                 105                 110
Thr Met Lys Thr Thr Val Thr Val Asp Asp Val Thr Ala Ile Arg Asn
        115                 120                 125
Tyr Lys Arg Leu
    130

<210> SEQ ID NO 25
<211> LENGTH: 126
<212> TYPE: PRT
<213> ORGANISM: Fasciola gigantica

<400> SEQUENCE: 25

Ser Trp Lys Tyr Gly Asp Ser Glu Asn Met Glu Ala Tyr Leu Lys Lys
1               5                   10                  15
Leu Gly Ile Ser Ser Asp Met Val Asp Lys Ile Leu Asn Ala Lys Pro
            20                  25                  30

Glu Phe Thr Phe Thr Leu Glu Gly Asn Gln Met Thr Ile Lys Met Val
        35                  40                  45

Ser Ser Leu Lys Thr Lys Ile Thr Thr Phe Thr Phe Gly Glu Glu Phe
    50                  55                  60

Glu Glu Glu Thr Pro Asp Gly Lys Lys Val Met Thr Lys Val Thr Lys
65                  70                  75                  80
Asp Ser Glu Ser Lys Met Thr Gln Val Ile Lys Gly Pro Glu Cys Ile
                85                  90                  95

Thr Glu Val Val Arg Glu Val Val Gly Asp Lys Met Ile Ala Thr Trp
            100                 105                 110
Thr Val Gly Asp Val Lys Ala Val Thr Thr Leu Leu Lys Ala
        115                 120                 125

<210> SEQ ID NO 26
<211> LENGTH: 133
<212> TYPE: PRT
<213> ORGANISM: Echinococcus granulosus

<400> SEQUENCE: 26

Met Glu Ala Phe Leu Gly Thr Trp Lys Met Glu Lys Ser Glu Gly Phe
1               5                   10                  15

Asp Lys Ile Met Glu Arg Leu Gly Val Asp Phe Val Thr Arg Lys Met
            20                  25                  30

Gly Asn Leu Val Lys Pro Asn Leu Ile Val Thr Asp Leu Gly Gly Gly
        35                  40                  45

Lys Tyr Lys Met Arg Ser Glu Ser Thr Phe Lys Thr Thr Glu Cys Ser
    50                  55                  60

Phe Lys Leu Gly Glu Lys Phe Lys Glu Val Thr Arg Phe Thr Arg Gly
65                  70                  75                  80

His Phe Phe Met Ile Thr Val Glu Asn Gly Val Met Lys His Glu Gln
                85                  90                  95

Asp Asp Lys Thr Lys Val Thr Tyr Ile Glu Arg Val Val Glu Gly Asn
            100                 105                 110
```

Glu Leu Lys Ala Thr Val Lys Val Asp Glu Val Val Cys Val Arg Thr
            115                 120                 125

Tyr Ser Lys Val Ala
    130

<210> SEQ ID NO 27
<211> LENGTH: 134
<212> TYPE: PRT
<213> ORGANISM: Homo sapiens

<400> SEQUENCE: 27

Pro Val Ser Phe Asn Gly Tyr Trp Lys Met Leu Ser Asn Glu Asn Phe
1               5                   10                  15

Glu Glu Tyr Leu Arg Ala Leu Asp Val Asn Val Ala Leu Arg Lys Ile
            20                  25                  30

Ala Asn Leu Leu Lys Pro Asp Lys Glu Ile Val Gln Asp Gly Asp His
            35                  40                  45

Met Ile Ile Arg Thr Leu Ser Thr Phe Arg Asn Tyr Ile Met Asp Phe
50                  55                  60

Gln Val Gly Lys Glu Phe Glu Glu Asp Leu Thr Gly Ile Asp Asp Arg
65                  70                  75                  80

Lys Cys Met Thr Thr Val Ser Trp Asp Gly Asp Lys Leu Gln Cys Val
                85                  90                  95

Gln Lys Gly Glu Lys Glu Gly Arg Gly Trp Thr Gln Trp Ile Glu Gly
            100                 105                 110

Asp Glu Leu His Leu Glu Met Arg Ala Glu Gly Val Thr Cys Lys Gln
            115                 120                 125

Val Phe Lys Lys Val His
130

<210> SEQ ID NO 28
<211> LENGTH: 132
<212> TYPE: PRT
<213> ORGANISM: Homo sapiens

<400> SEQUENCE: 28

Met Ala Phe Asp Gly Thr Trp Lys Val Asp Arg Asn Glu Asn Tyr Glu
1               5                   10                  15

Lys Phe Met Glu Lys Met Gly Ile Asn Val Val Lys Arg Lys Leu Gly
            20                  25                  30

Ala His Asp Asn Leu Lys Leu Thr Ile Thr Gln Glu Gly Asn Lys Phe
            35                  40                  45

Thr Val Lys Glu Ser Ser Asn Phe Arg Asn Ile Asp Val Val Phe Glu
50                  55                  60

Leu Gly Val Asp Phe Ala Tyr Ser Leu Ala Asp Gly Thr Glu Leu Thr
65                  70                  75                  80

Gly Thr Trp Thr Met Glu Gly Asn Lys Leu Val Gly Lys Phe Lys Arg
                85                  90                  95

Val Asp Asn Gly Lys Glu Leu Ile Ala Val Arg Glu Ile Ser Gly Asn
            100                 105                 110

Glu Leu Ile Gln Thr Tyr Thr Tyr Glu Gly Val Glu Ala Lys Arg Ile
            115                 120                 125

Phe Lys Lys Glu
130

<210> SEQ ID NO 29
<211> LENGTH: 133

```
<212> TYPE: PRT
<213> ORGANISM: Schistosoma gregaria

<400> SEQUENCE: 29

Val Lys Glu Phe Ala Gly Ile Lys Tyr Lys Leu Asp Ser Gln Thr Asn
1               5                   10                  15

Phe Glu Glu Tyr Met Lys Ala Ile Gly Val Gly Ala Ile Glu Arg Lys
                20                  25                  30

Ala Gly Leu Ala Leu Ser Pro Val Ile Glu Leu Glu Ile Leu Asp Gly
            35                  40                  45

Asp Lys Phe Lys Leu Thr Ser Lys Thr Ala Ile Lys Asn Thr Glu Phe
        50                  55                  60

Thr Phe Lys Leu Gly Glu Glu Phe Asp Glu Glu Thr Leu Asp Gly Arg
65                  70                  75                  80

Lys Val Lys Ser Thr Ile Thr Gln Asp Gly Pro Asn Lys Leu Val His
                85                  90                  95

Glu Gln Lys Gly Asp His Pro Thr Ile Ile Ile Arg Glu Phe Ser Lys
            100                 105                 110

Glu Gln Cys Val Ile Thr Ile Lys Leu Gly Asp Leu Val Ala Thr Arg
        115                 120                 125

Ile Tyr Lys Ala Gln
        130

<210> SEQ ID NO 30
<211> LENGTH: 131
<212> TYPE: PRT
<213> ORGANISM: Manduca sexta

<400> SEQUENCE: 30

Ser Tyr Leu Gly Lys Val Tyr Ser Leu Val Lys Gln Glu Asn Phe Asp
1               5                   10                  15

Gly Phe Leu Lys Ser Ala Gly Leu Ser Asp Asp Lys Ile Gln Ala Leu
                20                  25                  30

Val Ser Asp Lys Pro Thr Gln Lys Met Glu Ala Asn Gly Asp Ser Tyr
            35                  40                  45

Ser Asn Thr Ser Thr Gly Gly Gly Ala Lys Thr Val Ser Phe Lys
        50                  55                  60

Ser Gly Val Glu Phe Asp Asp Val Ile Gly Ala Gly Asp Ser Val Lys
65                  70                  75                  80

Ser Met Tyr Thr Val Asp Gly Asn Val Val Thr His Val Val Lys Gly
                85                  90                  95

Asp Ala Gly Val Ala Thr Phe Lys Lys Glu Tyr Asn Gly Asp Asp Leu
            100                 105                 110

Val Val Thr Ile Thr Ser Ser Asn Trp Asp Gly Val Ala Arg Arg Tyr
        115                 120                 125

Tyr Lys Ala
    130
```